US011981958B1

(12) United States Patent
Galonska

(10) Patent No.: US 11,981,958 B1
(45) Date of Patent: *May 14, 2024

(54) METHODS FOR SPATIAL ANALYSIS USING DNA CAPTURE

(71) Applicant: 10x Genomics, Inc., Pleasanton, CA (US)

(72) Inventor: Christina Galonska, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 17/406,824

(22) Filed: Aug. 19, 2021

Related U.S. Application Data

(60) Provisional application No. 63/068,146, filed on Aug. 20, 2020.

(51) Int. Cl.
*C12Q 1/6827* (2018.01)
*C12Q 1/6876* (2018.01)

(52) U.S. Cl.
CPC .......... *C12Q 1/6827* (2013.01); *C12Q 1/6876* (2013.01); *C12Q 2600/156* (2013.01)

(58) Field of Classification Search
CPC ............... C12Q 1/6827; C12Q 1/6876; C12Q 2600/156
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 4,988,617 A | 1/1991 | Landegren et al. | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,641,658 A | 6/1997 | Adams | |
| 5,648,245 A | 7/1997 | Fire et al. | |
| 5,658,751 A | 8/1997 | Yue | |
| 5,695,940 A | 12/1997 | Drmanac et al. | |
| 5,750,341 A | 5/1998 | Macevicz | |
| 5,763,175 A | 6/1998 | Brenner | |
| 5,830,711 A | 11/1998 | Barany et al. | |
| 5,837,832 A | 11/1998 | Chee et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 5,925,545 A | 7/1999 | Reznikoff et al. | |
| 5,928,906 A | 7/1999 | Koester et al. | |
| 5,958,775 A | 9/1999 | Wickstrrom | |
| 5,965,443 A | 10/1999 | Reznikoff et al. | |
| 6,013,440 A | 1/2000 | Lipshutz | |
| 6,027,889 A | 2/2000 | Barany et al. | |
| 6,054,274 A | 4/2000 | Sampson et al. | |
| 6,060,240 A | 5/2000 | Kamb et al. | |
| 6,130,073 A | 10/2000 | Eggerding | |
| 6,143,496 A | 11/2000 | Brown | |
| 6,153,389 A | 11/2000 | Haarer | |
| 6,159,736 A | 12/2000 | Reznikoff et al. | |
| 6,165,714 A | 12/2000 | Lane et al. | |
| 6,210,891 B1 | 4/2001 | Nyren | |
| 6,210,894 B1 | 4/2001 | Brennan | |
| 6,214,587 B1 | 4/2001 | Dattagupta | |
| 6,251,639 B1 | 6/2001 | Kurn | |
| 6,258,568 B1 | 7/2001 | Nyren | |
| 6,266,459 B1 | 7/2001 | Walt | |
| 6,268,148 B1 | 7/2001 | Barany et al. | |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.

Belton et al., "Hi-C: A comprehensive technique to capture the conformation of genomes," Methods, Nov. 2012, 58(3):268-276, 16 pages.

Bentzen et al., "Large-scale detection of antigen-specific T cells using peptide-MHC-I multimers labeled with DNA barcodes," Nat Biotechnol., Oct. 2016, 34(10):1037-1045, 12 pages.

Fan et al., "Illumina Universal Bead Arrays," Methods in Enzymology, 2006, 410:57-73.

(Continued)

*Primary Examiner* — Narayan K Bhat

(74) *Attorney, Agent, or Firm* — Fish & Richardson P.C.

(57) ABSTRACT

Provided herein are methods of detecting an analyte of interest to interrogate spatial gene expression in a sample using DNA templated ligation. For example, provided herein are methods for detecting an gDNA analyte in a biological sample where (i) the first RTL probe and second RTL probe hybridize to adjacent sequences on the gDNA analyte, (ii) enzyme-mediate cleavage of a 5' FLAP results in release of the 5' FLAP, and (iii) the sequence of the 5' FLAP is determined and used to detect the gDNA analyte in the biological sample.

18 Claims, 10 Drawing Sheets

(56) References Cited

U.S. PATENT DOCUMENTS

| | | |
|---|---|---|
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Eijk |
| 9,694,361 B2 | 7/2017 | Bharadwaj |

(56) References Cited

U.S. PATENT DOCUMENTS

| | | |
|---|---|---|
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 * | 3/2023 | Galonska ............. C12Q 1/6813 |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |

(56) References Cited

U.S. PATENT DOCUMENTS

| | | |
|---|---|---|
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |

(56) References Cited

U.S. PATENT DOCUMENTS

| | | |
|---|---|---|
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0105808 A1 | 4/2018 | Mikkelsen et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |

(56) References Cited

U.S. PATENT DOCUMENTS

| | | |
|---|---|---|
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1* | 7/2023 | Galonska .............. C12Q 1/6813 435/6.11 |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |

(56) References Cited

U.S. PATENT DOCUMENTS

| | | | |
|---|---|---|---|
| 2024/0026445 | A1 | 1/2024 | Ramachandran Iyer et al. |
| 2024/0035937 | A1 | 2/2024 | Cox et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |

(56) References Cited

FOREIGN PATENT DOCUMENTS

| | | |
|---|---|---|
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |

OTHER PUBLICATIONS

Hadrup et al., "Parallel detection of antigen-specific T-cell responses by multidimensional encoding of MHC multimers," Nat. Methods., Jul. 2009, 6(7), 520-526.

Mamedov et al., "Preparing unbiased T-cell receptor and antibody cDNA libraries for the deep next generation sequencing profiling," Frontiers in Immunol., Dec. 23, 2013, 4(456):1-10.

Oksuz et al., "Systematic evaluation of chromosome conformation capture assays," Nature Methods, Sep. 2021, 18:1046-1055.

Rohland et al., "Partial uracil-DNA-glycosylase treatment for screening of ancient DNA," Phil. Trans. R. Soc. B, Jan. 19, 2015, 370(1660): 20130624, 11 pages.

Su et al., "Restriction enzyme selection dictates detection range sensitivity in chromatin conformation capture-based variant-to-gene mapping approaches," bioRxiv, Dec. 15, 2020, 22 pages.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Ergin et al., "Proteomic Analysis of PAXgene-Fixed Tissues," J Proteome Res., 2010, 9(10):5188-96.

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.

Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.

U.S. Appl. No. 16/353,937, filed Mar. 14, 2019, Frisen et al.

U.S. Appl. No. 17/707,189, filed Mar. 29, 2022, Chell et al.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.

(56) References Cited

OTHER PUBLICATIONS

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal GâT Mismatches in DNA," Biochemistry, 1996, 36(34):10581-10594.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Andresen et al., "Helicase-dependent amplification: use in OnChip amplification and potential for point-of-care diagnostics," Expert Rev Mol Diagn., Oct. 2009, 9(7):645-650.

Aran et al., "xCell: digitally portraying the tissue cellular heterogeneity landscape," Genome Biol., Nov. 2017, 18(1):220, 14 pages.

Archer et al., "Selective and flexible depletion of problematic sequences from RNA-seq libraries at the cDNA stage," BMC Genomics, May 2014, 15(1):401, 9 pages.

Armani et al, "2D-PCR: a method of mapping DNA in tissue sections," Lab Chip, 2009, 9(24):3526-34.

Asp et al., "Spatially Resolved Transcriptomes—Next Generation Tools for Tissue Exploration," Bioessays, Oct. 2020, 42(10):e1900221, 16 pages.

Atkinson et al., "An Updated Protocol for High Throughput Plant Tissue Sectioning," Front Plant Sci, 2017, 8:1721, 8 pages.

Atkinson, "Overview of Translation: Lecture Manuscript," U of Texas, 2000, DD, pp. 6.1-6.8.

Bains et al., "A novel method for nucleic acid sequence determination," Journal of Theoretical Biology, 1988, 135(3), 303-7.

Balakrishnan et al., "Flap endonuclease 1," Annu Rev Biochem., Jun. 2013, 82:119-138.

Barnes, "PCR amplification of up to 35-kb DNA with high fidelity and high yield from lambda bacteriophage templates," Proc. Natl. Acad. Sci USA, 1994, 91(6):2216-2220.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Bartosovic et al., "Single-cell CUT&Tag profiles histone modifications and transcription factors in complex tissues," Nat Biotechnol., Jul. 2021, 39(7):825-835, Abstract.

Baugh et al., "Quantitative analysis of mRNA amplification by in vitro transcription," Nucleic Acids Res., 2001, 29(5):e29, 9 pages.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

Bell, "A simple way to treat PCR products prior to sequencing using ExoSAP-IT," Biotechniques, 2008, 44(6):834, 1 page.

Bentley et al., "Accurate whole human genome sequencing using reversible terminator chemistry," Nature, 2008, 456(7218):53-59.

Bergenståhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Birney et al., "Identification and analysis of functional elements in 1% of the human genome by the ENCODE pilot project," Nature, 2007, 447(7146):799-816.

Blair et al., "Microarray temperature optimization using hybridization kinetics," Methods Mol Biol., 2009, 529:171-96.

Blanchard et al., "High-density oligonucleotide arrays," Biosensors & Bioelectronics, 1996, 11(6-7):687-690.

Blanco et al., "A practical approach to FRET-based PNA fluorescence in situ hybridization," Methods, Dec. 2010, 52(4):343-51.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolotin et al., "MiXCR: software for comprehensive adaptive immunity profiling," Nat Methods., May 2015, 12(5):380-1.

Boulé et al., "Terminal deoxynucleotidyl transferase indiscriminately incorporates ribonucleotides and deoxyribonucleotides," J Biol Chem., Aug. 2001, 276(33):31388-93.

Brandon et al., "Mitochondrial mutations in cancer," Oncogene, 2006, 25(34):4647-4662.

Brenner et al., "Gene expression analysis by massively parallel signature sequencing (MPSS) on microbead arrays," Nat. Biotech., 2000, 18(6):630-634.

Brenner et al., "In vitro cloning of complex mixtures of DNA on microbeads: physical separation of differentially expressed cDNAs," Proc. Natl. Acad. Sci. USA, 2000, 97(4):1665-1670.

Brow, "35—The Cleavase I enzyme for mutation and polymorphism scanning," PCR Applications Protocols for Functional Genomics, 1999, pp. 537-550.

Brown et al., "Retroviral integration: structure of the initial covalent product and its precursor, and a role for the viral IN protein," Proc Natl Acad Sci USA, Apr. 1989, 86(8):2525-9.

Buenrostro et al., "Transposition of native chromatin for multimodal regulatory analysis and personal epigenomics," Nat Methods, Dec. 2013, 10(12):1213-1218.

Bullard et al., "Direct comparison of nick-joining activity of the nucleic acid ligases from bacteriophage T4," Biochem. J. 2006, 398(1):135-144.

Burgess, "A space for transcriptomics," Nature Reviews Genetics, 2016, 17(8):436-7.

Burgess, "Finding structure in gene expression," Nature Reviews Genetics, 2018, 19(5):249, 1 page.

Burgess, "Spatial transcriptomics coming of age," Nat Rev Genet., Jun. 2019, 20(6):317, 1 page.

(56) References Cited

OTHER PUBLICATIONS

Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Evers et al., "The effect of formaldehyde fixation on RNA: optimization of formaldehyde adduct removal," J Mol Diagn., May 2011, 13(3):282-8.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.

(56) References Cited

OTHER PUBLICATIONS

Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.

(56) References Cited

OTHER PUBLICATIONS

Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans- chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.

(56) References Cited

OTHER PUBLICATIONS

Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/EP2016/057355, dated Oct. 10, 2017, 7 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Preliminary Report on Patentability in International Appln. No. PCT/US2021/018795, dated Sep. 1, 2022, 10 pages.
PCT International Preliminary Report on Patentability in International Appln. No. PCT/US2021/018816, dated Sep. 1, 2022, 9 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
PCT International Search Report and Written Opinion in International Appln. No. PCT/US2022/028071, dated Aug. 25, 2022, 13 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.

(56) References Cited

OTHER PUBLICATIONS

Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.

(56) References Cited

OTHER PUBLICATIONS

Wang et al., "Imaging-based pooled CRISPR screening reveals regulators of lncRNA localization," Proc Natl Acad Sci USA, May 2019, 116(22):10842-10851.

Wang et al., "Optimization of Process Conditions for Infected Animal Tissues by Alkaline Hydrolysis Technology," Procedia Environmental Sciences, 2016, 31:366-374.

Wang et al., "Tagmentation-based whole-genome bisulfite sequencing," Nature Protocols, Oct. 2013, 8(10):2022-2032.

Wang et al., "High-fidelity mRNA amplification for gene profiling," Nature Biotechnology, Apr. 2000, 18(4):457-459.

Wang, "RNA amplification for successful gene profiling analysis," J Transl Med., Jul. 2005, 3:28, 11 pages.

Weinreich et al., "Evidence that the cis Preference of the Tn5 Transposase is Caused by Nonproductive Multimerization," Genes and Development, Oct. 1994, 8(19):2363-2374.

Wiedmann et al., "Ligase chain reaction (LCR)—overview and applications," PCR Methods Appl., Feb. 1994, 3(4):S51-64.

Wilson et al., "New transposon delivery plasmids for insertional mutagenesis in Bacillus anthracis," J Microbiol Methods, Dec. 2007, 71(3):332-5.

Wohnhaas et al., "DMSO cryopreservation is the method of choice to preserve cells for droplet-based single-cell RNA sequencing," Scientific Reports, Jul. 2019, 9(1):10699, 14 pages.

Wolf et al., "Rapid hybridization kinetics of DNA attached to submicron latex particles," Nucleic Acids Res, 1987, 15(7):2911-2926.

Wong et al., "Direct Site-Selective Covalent Protein Immobilization Catalyzed by a Phosphopantetheinyl Transferase," J. Am. Chem Soc., 2008, 130(37):12456-64.

Worthington et al., "Cloning of random oligonucleotides to create single-insert plasmid libraries," Anal Biochem, 2001, 294(2):169-175.

Wu et al., "Detection DNA Point Mutation with Rolling-Circle Amplification Chip," IEEE, 2010 4th International Conference on Bioinformatics and Biomedical Engineering, Jun. 2010, 4 pages.

Wu et al., "RollFISH achieves robust quantification of single-molecule RNA biomarkers in paraffin-embedded tumor tissue samples," Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Yeakley et al., "A trichostatin A expression signature identified by TempO-Seq targeted whole transcriptome profiling," PLoS One, May 2017, 12(5):e0178302, 22 pages.

Yeakley et al., "Profiling alternative splicing on fiber-optic arrays," Nature biotechnology, 2002, 20:353-358.

Yershov et al., "DNA analysis and diagnostics on oligonucleotide microchips," Proc. Natl. Acad. Sci. USA, May 1996, 93(10):4913-4918.

Yin et al., "Genetically encoded short peptide tag for versatile protein labeling by Sfp phosphopantetheinyl transferase," PNAS, 2005, 102(44):15815-20.

Zhang et al., "Archaeal RNA ligase from Thermoccocus kodakarensis for template dependent ligation," RNA Biol., Jan. 2017, 14(1):36-44.

Zhang et al., "Assembling DNA through Affinity Binding to Achieve Ultrasensitive Protein Detection," Angew Chem Int Ed Engl., 2013, 52(41):10698-705.

Zhang et al., "Binding-induced DNA assembly and its application to yoctomole detection of proteins," Anal Chem, 2012, 84(2):877-884.

Zhang et al., "Genome-wide open chromatin regions and their effects on the regulation of silk protein genes in Bombyx mori," Sci Rep., Oct. 2017, 7(1):12919, 9 pages.

Zhang et al., "Multiplex ligation-dependent probe amplification (MLPA) for ultrasensitive multiplexed microRNA detection using ribonucleotide-modified DNA probes†," Chem. Commun., 2013, 49:10013-10015.

Zhao et al., "Isothermal Amplification of Nucleic Acids," Chemical Reviews, Nov. 2015, 115(22):12491-12545.

Zheng et al., "Origins of human mitochondrial point mutations as DNA polymerase gamma-mediated errors," Mutat. Res., 2006, 599(1-2):11-20.

Zhou et al., "Genetically encoded short peptide tags for orthogonal protein labeling by Sfp and AcpS phosphopantetheinyl transferases," ACS Chemical Biol., 2007, 2(5):337-346.

Zhu et al., "Reverse transcriptase template switching: a SMART approach for full-length cDNA library construction," Biotechniques, Apr. 2001, 30(4):892-897.

U.S. Appl. No. 63/033,348, filed Jun. 2, 2020, Bent.

Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.

Baner et al., "Signal amplification of padlock probes by rolling circle replication," Nucleic Acids Res., 1998, 26(22):5073-5078.

Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).

Chen et al., "Efficient in situ barcode sequencing using padlock probe-based BaristaSeq," Nucleic Acids Res., 2018, 46(4): e22, 11 pages.

Codeluppi et al., "Spatial organization of the somatosensory cortex revealed by osmFISH," Nature Methods, Nov. 2018, 15:932-935.

Dean et al., "Rapid Amplification Of Plasmid And Phage DNA Using Phi29 DNA Polymerase And Multiply-Primed Rolling Circle Amplification," Genome Research, Jun. 2001, 11:1095-1099.

Eng et al., "Transcriptome-scale super-resolved imaging in tissues by RNA seqFISH+," Nature, Apr. 2019, 568(7751):235-239, 37 pages.

Faruqi et al., "High-throughput genotyping of single nucleotide polymorphisms with rolling circle amplification," BMC Genomics, Aug. 2001, 2:4, 10 pages.

Gao et al., "A highly homogeneous expansion microscopy polymer composed of tetrahedron-like monomers," bioRxiv, Oct. 22, 2019, 23 pages (Preprint).

Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.

Goh et al., "Highly Specific Multiplexed RNA Imaging In Tissues With Split-FISH," Nat Methods, Jun. 15, 2020, 17(7):689-693, 21 pages.

Goransson et al., "A single molecule array for digital targeted molecular analyses," Nucleic Acids Res., Nov. 25, 2009, 37(1):e7, 9 pages.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788592, Oct. 14, 2020, 39 pages.

Mignardi et al., "Oligonucleotide gap-fill ligation for mutation detection and sequencing in situ," Nucleic Acids Research, Aug. 3, 2015, 43(22):e151, 12 pages.

Mohsen et al., "The Discovery of Rolling Circle Amplification and Rolling Circle Transcription," Acc Chem Res., Nov. 15, 2016, 49(11):2540-2550, 25 pages.

Nallur et al., "Signal amplification by rolling circle amplification on DNA microarrays," Nucleic Acids Res., Dec. 1, 2001, 29(23):e118, 9 pages.

Raj et al., "Imaging individual mRNA molecules using multiple singly labeled probes," Nature Methods, Oct. 2008, 5(10):877-879, 9 pages.

Schweitzer et al., "Immunoassays with rolling circle DNA amplification: A versatile platform for ultrasensitive antigen detection," Proc. Natl. Acad. Sci. USA, May 22, 2000, 97:10113-119.

(56) References Cited

OTHER PUBLICATIONS

Takei et al., "Integrated Spatial Genomics Reveals Global Architecture Of Single Nuclei," Nature, Jan. 27, 2021, 590(7845):344-350, 53 pages.
Bibikova et al., "Quantitative gene expression profiling in formalin-fixed paraffin-embedded tissues using universal bead arrays," The American Journal of Pathology, Nov. 1, 2004, 165(5):1799-1807.
Chen et al. "Arrayed profiling of multiple glycans on whole living cell surfaces." Analytical chemistry, Oct. 15, 2013, 85(22):11153-11158.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
Marx, "Method of the Year: spatially resolved transcriptomics," Nature Methods, 2021, 18(1):9-14.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
Hobro et al, "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Schmidl et al., "ChIPmentation: fast, robust, low-input ChIP-seq for histones and transcription factors," Nature Methods, Oct. 2015, 12:963-965.

\* cited by examiner

METHODS FOR SPATIAL ANALYSIS USING DNA CAPTURE

CROSS-REFERENCE TO RELATED APPLICATIONS

This application claims priority to U.S. Provisional Patent Application No. 63/068,146, filed Aug. 20, 2020. The entire content of the foregoing application is incorporated herein by reference.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Spatial analysis takes advantage of targeting a particular analyte in a sample using a capture probe that includes a capture domain capable of capturing the particular analyte. In the context of RNA, one approach developed to enhance resolution of spatial analysis is a process called RNA-templated ligation (RTL), which includes multiple oligonucleotides targeting adjacent or nearby complementary sequences on the analyte (e.g., RNA). RTL methods have not been adapted to different types of nucleic acid analytes in the context of spatial analysis. Thus, there remains a need to adapt RTL methods to the spatial analysis of a genomic DNA (gDNA) molecule.

SUMMARY

Featured herein are methods of identifying a target gDNA analyte of interest or a genetic variant in a gDNA analyte. In particular, methods provided herein co-opt traditional RTL principles to include oligonucleotide probes that hybridize to adjacent complementary genomic DNA (gDNA) sequences. Methods provided herein allow a readout of a DNA-templated hybridization event that does not require single stranded DNA from the DNA-DNA template. For example, an oligonucleotide (e.g., a second RTL probe) that hybridizes to the gDNA analyte includes a 5' FLAP sequence that can be removed and detected upon an enzyme-mediated cleavage event that does not require removal of the hybridized oligonucleotide probes. Detection of the 5' FLAP provides a readout for the DNA-templated hybridization event, which can serve as a proxy for detecting a gDNA analyte or a genetic variant within a gDNA analyte.

In one aspect, the disclosure features a method for determining the abundance and/or location of a genomic DNA (gDNA) analyte in a biological sample, the method comprising: (a) contacting the biological sample with a substrate comprising a plurality of capture probes, wherein a capture probe of the plurality comprises a spatial barcode and a capture domain; (b) contacting the biological sample with a first RTL probe and a second RTL probe, wherein the first RTL probe and the second RTL probe are substantially complementary to adjacent sequences of the gDNA analyte, and wherein the second RTL probe comprises a 5' FLAP; (c) hybridizing the first RTL probe and the second RTL probe to the gDNA analyte; (d) cleaving the second RTL probe, thereby releasing the 5' FLAP; (e) hybridizing the 5' FLAP to the capture domain; and (f) determining (i) all or a part of the sequence of the 5' FLAP, or a complement thereof, and (ii) all or a part of the sequence of the spatial barcode, or a complement thereof, and using the determined sequence of (i) and (ii) to identify the abundance and/or location of the gDNA analyte in the biological sample.

In some embodiments, the first RTL probe and the second RTL probes are DNA probes.

In some embodiments, the 5' FLAP comprises a first barcode sequence, wherein the first barcode sequence comprises a sequence that identifies the first RTL probe, the second RTL probe, the gDNA analyte, or any combination thereof.

In some embodiments, the 5' FLAP comprises (i) a functional sequence, wherein the functional sequence is a primer sequence, and (ii) a capture probe binding domain, wherein the capture probe binding domain comprises a homopolymeric sequence or a poly(A) sequence.

In some embodiments, the cleaving the second RTL probe comprises providing an endonuclease, wherein the endonuclease cleaves a portion of the first RTL probe, a portion of second RTL probe, the 5' FLAP of the second RTL probe, or any combination thereof.

In some embodiments, the determining step comprises sequencing all or part of the 5' FLAP.

In some embodiments, the biological sample is a formalin-fixed, paraffin-embedded (FFPE) sample.

In another aspect, the disclosure features a method of detecting a genetic variant in a gDNA analyte in a biological sample, the method comprising: (a) contacting the biological sample with a substrate comprising a plurality of capture probes, wherein a capture probe of the plurality comprises a spatial barcode and a capture domain; (b) contacting the biological sample with a first RTL probe and a second RTL probe, wherein the first RTL probe and the second RTL probe each comprise a sequence that is substantially complementary to adjacent sequences of the gDNA analyte; wherein the first RTL probe and the second RTL probe are capable of forming an invasive cleavage structure in the presence of the genetic variant; and wherein the second RTL probe further comprises a 5' FLAP; (c) hybridizing the first RTL probe and the second RTL probe to the gDNA analyte; (d) cleaving the second RTL probe when the genetic variant is present, thereby releasing the 5' FLAP; (e) hybridizing the 5' FLAP to the capture domain; and (f) determining (i) all or a part of the sequence of the 5' FLAP, or a complement thereof, and (ii) all or a part of the sequence of the spatial barcode, or a complement thereof, and using the determined sequence of (i) and (ii) to detect the genetic variant in the gDNA analyte in the biological sample.

In some embodiments, the genetic variant is a single nucleotide polymorphism (SNP) or a nucleotide point mutation, or wherein the genetic variant comprises at least two, at least three, at least four, at least five, or more genetic variants.

In some embodiments, the first RTL probe comprises a sequence that is substantially complementary to a sequence 3' to the genetic variant, or at least one nucleotide that is complementary to a wild-type sequence of the genetic variant.

In some embodiments, the second RTL probe comprises a sequence substantially complementary to a sequence 5' to the genetic variant, and/or a nucleotide that is complementary to the genetic variant.

In some embodiments, the 5' FLAP comprises a nucleotide that is complementary to the genetic variant.

In some embodiments, the first RTL probe and the second RTL probe are capable of forming an invasive cleavage structure in the presence of the genetic variant.

In some embodiments, the 5' FLAP comprises a capture probe binding domain, wherein the capture probe binding domain comprises a homopolymeric sequence or a poly(A) sequence.

In some embodiments, the 5' FLAP comprises from 5' to 3'; a functional sequence, a barcode, and a capture probe binding domain sequence.

In some embodiments, the 5' FLAP comprises from 5' to 3'; a functional sequence, a barcode, a capture probe binding domain sequence, and an additional nucleotide, wherein the additional nucleotide comprises a nucleotide that is complementary to the genetic variant or a nucleotide that is complementary to the wild type sequence of the genetic variant.

In some embodiments, the method further comprises providing a capture probe binding domain blocking moiety that interacts with the capture probe binding domain, wherein the method further comprises releasing the capture probe binding domain blocking moiety from the capture probe binding domain prior to contacting the biological sample with the substrate, wherein the capture probe binding domain blocking moiety comprises a poly-uridine sequence, a poly-thymidine sequence, or both, and wherein releasing the capture probe binding domain blocking moiety from the poly(A) sequence comprises denaturing the ligated probe.

In some embodiments, the biological sample is an FFPE sample.

In another aspect, the disclosure features a kit comprising: (a) a first RTL probe and a second RTL probe, wherein the first RTL probe and the second RTL probe are substantially complementary to adjacent sequences of a gDNA analyte, or wherein the first RTL probe and the second RTL probe each comprise a sequence that is substantially complementary to adjacent sequences of the gDNA analyte, and wherein the second RTL probe comprises a 5' FLAP; (b) an endonuclease, wherein the endonuclease cleaves the 5' FLAP thereby releasing the 5' FLAP from the second RTL probe; (c) a substrate comprising a plurality of capture probes, wherein a capture probe of the plurality comprises a spatial barcode and a capture domain; and (d) instructions for performing any one of the methods described herein.

In another aspect, the disclosure features a composition for determining the abundance and/or location of a gDNA analyte in a biological sample, wherein the composition comprises: a first RTL probe and a second RTL probe hybridized to the gDNA analyte, wherein the first RTL probe and the second RTL probe are substantially complementary to adjacent sequences of the gDNA analyte, or wherein the first RTL probe and the second RTL probe each comprise a sequence that is substantially complementary to adjacent sequences of the gDNA analyte, and wherein the second RTL probe comprises a 5' FLAP, wherein the 5' FLAP comprises a sequence that is capable of hybridizing to a capture domain of a capture probe.

In one aspect, this disclosure features methods for detecting a genomic DNA (gDNA) molecule in a biological sample, including: (a) contacting the biological sample with a first probe oligonucleotide and a second probe oligonucleotide, wherein the first probe oligonucleotide and the second probe oligonucleotide are substantially complementary to adjacent sequences of the gDNA molecule, and wherein the second probe oligonucleotide includes a 5' FLAP; (b) hybridizing the first probe oligonucleotide and the second probe oligonucleotide to the gDNA molecule; (c) cleaving the second probe oligonucleotide, thereby releasing the 5' FLAP; and (d) determining all or a part of the sequence of the 5' FLAP to detect the gDNA molecule.

In another aspect, this disclosure features methods of detecting a genetic variant in a gDNA molecule in a biological sample including: (a) contacting the biological sample with a first probe oligonucleotide and a second probe oligonucleotide, wherein the first probe oligonucleotide and the second probe oligonucleotide each include a sequence that is substantially complementary to adjacent sequences of the gDNA molecule; wherein the first probe oligonucleotide and the second probe oligonucleotide are capable of forming an invasive cleavage structure in the presence of the genetic variant; and wherein the second probe oligonucleotide further includes a 5' FLAP; (b) hybridizing the first probe oligonucleotide and the second probe oligonucleotide to the gDNA molecule; (c) cleaving the second probe oligonucleotide when the genetic variant is present, thereby releasing the 5' FLAP; and (d) determining all or a part of the sequence of the 5' FLAP to detect the genetic variant in the gDNA molecule.

In some embodiments, the gDNA molecule includes one or more single nucleotide variants compared to a reference gDNA molecule.

In some embodiments, the first probe oligonucleotide includes a sequence that is substantially complementary to a sequence 3' to the genetic variant. In some embodiments, the first probe oligonucleotide further includes at least one nucleotide that is complementary to a wild-type sequence of the genetic variant. In some embodiments, the first probe oligonucleotide includes at least two ribonucleic acid bases at the 3' end. In some embodiments, the first probe oligonucleotide includes at least two deoxyribonucleic acid bases at the 3' end.

In some embodiments, the second probe oligonucleotide includes a sequence substantially complementary to a sequence 5' to the genetic variant.

In some embodiments, the 5' FLAP further includes a first barcode sequence. In some embodiments, the first barcode sequence includes a sequence that identifies at least one of the first probe oligonucleotide, the second probe oligonucleotide, or the gDNA molecule.

In some embodiments, the 5' FLAP further includes a functional sequence. In some embodiments, the functional sequence is selected from a primer sequence, a Read 1 sequence, a Read 2 sequence, an index sequence, a P5 index sequence, and a P7 index sequence.

In some embodiments, the 5' FLAP further includes a nucleotide that is complementary to the genetic variant. In some embodiments, the second probe oligonucleotide further includes a second barcode.

In some embodiments, the second probe oligonucleotide includes a sequence that is complementary to a capture domain. In some embodiments, the second probe oligonucleotide further includes a nucleotide that is complementary to the genetic variant.

In some embodiments, the cleaving step includes providing an endonuclease. In some embodiments, the endonuclease cleaves the invasive cleavage structure.

In some embodiments, the endonuclease cleaves a portion of the first probe oligonucleotide. In some embodiments, the endonuclease cleaves the at least one nucleotide that is complementary to a wild-type sequence of the gDNA molecule of the first probe oligonucleotide. In some embodiments, the endonuclease cleaves a portion of second probe oligonucleotide. In some embodiments, the endonuclease cleaves the 5' FLAP of the second probe oligonucleotide. In some embodiments, the endonuclease is FLAP endonuclease 1 (FEN1).

In some embodiments, the method further includes contacting the biological sample with a permeabilization reagent.

In some embodiments, the biological sample is contacted with the permeabilization reagent before step (d) (e.g., determining all or a part of the sequence of the 5' FLAP to detect the gDNA molecule).

In some embodiments, the method further includes denaturing the gDNA under conditions wherein the first probe oligonucleotide and the second probe oligonucleotide can hybridize to the gDNA molecule.

In some embodiments, the determining step includes amplifying all or part of the 5' FLAP. In some embodiments, the amplifying is isothermal. In some embodiments, the amplifying is not isothermal. In some embodiments, the determining step includes sequencing.

In another aspect, this disclosure features methods for detecting a gDNA molecule at a spatial location in a biological sample, including: (a) contacting a biological sample with a first probe oligonucleotide and a second probe oligonucleotide, wherein the first probe oligonucleotide and the second probe oligonucleotide are substantially complementary to adjacent sequences of the gDNA molecule, and wherein the second probe oligonucleotide includes a 5' FLAP; (b) hybridizing the first probe oligonucleotide and the second probe oligonucleotide to the gDNA molecule; (c) cleaving the second probe oligonucleotide, thereby releasing the 5' FLAP; (d) contacting the biological sample with a substrate including a plurality of capture probes, wherein a capture probe of the plurality includes a spatial barcode and a capture domain; (e) hybridizing the 5' FLAP to the capture domain; and (f) determining (i) all or a part of the sequence of the 5' FLAP, or a complement thereof, and (ii) all or a part of the sequence of the spatial barcode, or a complement thereof, and using the determined sequence of (i) and (ii) to identify the spatial location of the gDNA molecule in the biological sample.

In another aspect, this disclosure features methods of detecting a genetic variant in a genomic DNA (gDNA) molecule at a spatial location in a biological sample including: (a) contacting the biological sample with a first probe oligonucleotide and a second probe oligonucleotide, wherein the first probe oligonucleotide and the second probe oligonucleotide each include a sequence that is substantially complementary to adjacent sequences of the gDNA molecule; wherein the first probe oligonucleotide and the second probe oligonucleotide are capable of forming an invasive cleavage structure in the presence of the genetic variant; and wherein the second probe oligonucleotide further includes a 5' FLAP; (b) hybridizing the first probe oligonucleotide and the second probe oligonucleotide to the gDNA molecule; (c) cleaving the second probe oligonucleotide when the genetic variant is present, thereby releasing the 5' FLAP; (d) contacting the biological sample with a substrate including a plurality of capture probes, wherein a capture probe of the plurality includes a spatial barcode and a capture domain; (e) hybridizing the cleavage product to the capture domain; and (f) determining (i) all or a part of the sequence of the 5' FLAP, or a complement thereof, and (ii) all or a part of the sequence of the spatial barcode, or a complement thereof, and using the determined sequence of (i) and (ii) to identify the spatial location of the gDNA molecule in the biological sample.

In some embodiments, the gDNA molecule includes one or more single nucleotide variants compared to a reference gDNA molecule.

In some embodiments, the first probe oligonucleotide includes a sequence that is substantially complementary to a sequence 3' of the genetic variant. In some embodiments, the first probe oligonucleotide further includes at least one nucleotide that is complementary to a wild-type sequence of the genetic variant. In some embodiments, the first probe oligonucleotide includes at least two ribonucleic acid bases at the 3' end. In some embodiments, the first probe oligonucleotide includes at least two deoxyribonucleic acid bases at the 3' end.

In some embodiments, the second probe oligonucleotide includes a sequence substantially complementary to a sequence 5' to the genetic variant.

In some embodiments, the 5' FLAP further includes a first barcode sequence. In some embodiments, the first barcode sequence includes a sequence that identifies at least one of the first probe oligonucleotide, the second probe oligonucleotide, or the gDNA molecule. In some embodiments, the first barcode sequence includes a sequence that identifies the gDNA molecule.

In some embodiments, the 5' FLAP further includes a functional sequence. In some embodiments, the functional sequence is selected from a primer sequence, a Read 1 sequence, a Read 2 sequence, an index sequence, a P5 index sequence, and a P7 index sequence.

In some embodiments, the 5' FLAP further includes a capture probe binding domain. In some embodiments, the capture probe binding domain includes a homopolymeric sequence. In some embodiments, the capture probe binding domain includes a poly(A) sequence. In some embodiments, the 5' FLAP further includes a nucleotide that is complementary to the genetic variant.

In some embodiments, the 5' FLAP includes from 5' to 3'; a functional sequence, a barcode, and a capture probe binding domain sequence. In some embodiments, the 5' FLAP includes from 5' to 3'; a functional sequence, a barcode, a capture probe binding domain sequence, and an additional nucleotide. In some embodiments, the additional nucleotide includes a nucleotide that is complementary to the genetic variant. In some embodiments, the additional nucleotide includes a nucleotide that is complementary to the wild type sequence of the genetic variant.

In some embodiments, the method further includes providing a capture probe binding domain blocking moiety that interacts with the capture probe binding domain.

In some embodiments, the method further includes releasing the capture probe binding domain blocking moiety from the capture probe binding domain prior to contacting the biological sample with the substrate. In some embodiments, the capture probe binding domain blocking moiety includes a poly-uridine sequence, a poly-thymidine sequence, or both. In some embodiments, releasing the capture probe binding domain blocking moiety from the poly(A) sequence includes denaturing the ligated probe.

In some embodiments, the second probe oligonucleotide further includes a second barcode.

In some embodiments, the second probe oligonucleotide further includes a second capture probe binding domain.

In some embodiments, the second probe oligonucleotide further includes a nucleotide that is complementary to the genetic variant.

In some embodiments, the cleaving step includes providing an endonuclease. In some embodiments, the endonuclease cleaves the invasive cleavage structure. In some embodiments, the endonuclease cleaves a portion of the first probe oligonucleotide. In some embodiments, the endonuclease cleaves the at least one nucleotide that is complementary to a wild-type sequence of the gDNA molecule of the first probe oligonucleotide. In some embodiments, the endonuclease cleaves a portion of second probe oligonucleotide. In some embodiments, the endonuclease cleaves the 5' FLAP of the second probe oligonucleotide. In some embodiments, the endonuclease is FLAP endonuclease 1 (FEN1).

In some embodiments, the method further includes contacting the biological sample with a permeabilization reagent. In some embodiments, the biological sample is contacted with the permeabilization reagent before step (d) (e.g., contacting the biological sample with a substrate including a plurality of capture).

In some embodiments, the method further includes denaturing the gDNA under conditions wherein the first probe oligonucleotide and the second probe oligonucleotide can hybridize to the gDNA molecule.

In some embodiments, the determining step includes amplifying all or part of the 5' FLAP specifically bound to the capture domain. In some embodiments, the amplifying is isothermal. In some embodiments, the amplifying is not isothermal. In some embodiments, the determining step includes sequencing.

In some embodiments of any of the methods for detecting a genetic variant in a gDNA molecule, the genetic variant is a single nucleotide polymorphism (SNP). In some embodiments of any of the methods for detecting a genetic variant in a gDNA molecule, the genetic variant is a nucleotide point mutation. In some embodiments of any of the methods for detecting a genetic variant in a gDNA molecule, the genetic variant includes at least two, at least three, at least four, at least five, or more genetic variants.

In some embodiments, the first probe oligonucleotide is at least 70%, at least 75%, at least 80%, at least 85%, at least 90%, at least 95%, at least 96%, at least 97%, at least 98%, at least 99%, or 100% complementary to a sequence of the gDNA molecule. In some embodiments, the second probe oligonucleotide is at least 70%, at least 75%, at least 80%, at least 85%, at least 90%, at least 95%, at least 96%, at least 97%, at least 98%, at least 99%, or 100% complementary to a sequence of the gDNA molecule.

In some embodiments, the biological sample is a formalin-fixed, paraffin-embedded (FFPE), frozen, or fresh sample. In some embodiments, the biological sample is a FFPE sample.

In another aspect, this disclosure features a kit for use in a method of detecting analyte in a biological sample, wherein the kit includes any two or more of: (a) a first probe oligonucleotide and a second probe oligonucleotide, wherein the first probe oligonucleotide and the second probe oligonucleotide are substantially complementary to adjacent sequences of the analyte, and wherein the second probe oligonucleotide includes a 5' FLAP; (b) an endonuclease, wherein the endonuclease cleaves the 5' FLAP thereby releasing the 5' FLAP from the second probe oligonucleotide; (c) a substrate including a plurality of capture probes, wherein a capture probe of the plurality includes a spatial barcode and a capture domain, wherein the 5' FLAP is capable of hybridizing to the capture domain; and (d) instructions for carrying out any of the methods described herein.

In another aspect, this disclosure features a kit for use in a method of detecting analyte in a biological sample, wherein the kit includes any two or more of: (a) a first probe oligonucleotide and a second probe oligonucleotide, wherein the first probe oligonucleotide and the second probe oligonucleotide are substantially complementary to adjacent sequences of the analyte, and wherein the second probe oligonucleotide includes a 5' FLAP; (b) an endonuclease, wherein the endonuclease cleaves the 5' FLAP thereby releasing the 5' FLAP from the second probe oligonucleotide; and (c) instructions for carrying out any of the methods described herein.

In another aspect, this disclosure features a kit for use in a method of detecting a genetic variant in an gDNA molecule in a biological sample, wherein the kit includes any two or more of: (a) a first probe oligonucleotide and a second probe oligonucleotide, wherein the first probe oligonucleotide and the second probe oligonucleotide each include a sequence that is substantially complementary to adjacent sequences of the gDNA molecule; wherein the first probe oligonucleotide and the second probe oligonucleotide are capable of forming an invasive cleavage structure in the presence of the genetic variant; and wherein the second probe oligonucleotide further includes a 5' FLAP; (b) an endonuclease, wherein the endonuclease cleaves the 5' FLAP thereby releasing the 5' FLAP from the second probe oligonucleotide; (c) a substrate including a plurality of capture probes, wherein a capture probe of the plurality includes a spatial barcode and a capture domain, wherein the 5' FLAP is capable of hybridizing to the capture domain; and (d) instructions for carrying out any of the methods described herein.

In another aspect, this disclosure features a kit for use in a method of detecting a genetic variant in an gDNA molecule in a biological sample, wherein the kit includes any two or more of: (a) a first probe oligonucleotide and a second probe oligonucleotide, wherein the first probe oligonucleotide and the second probe oligonucleotide each include a sequence that is substantially complementary to adjacent sequences of the gDNA molecule; wherein the first probe oligonucleotide and the second probe oligonucleotide are capable of forming an invasive cleavage structure in the presence of the genetic variant; and wherein the second probe oligonucleotide further includes a 5' FLAP; (b) an endonuclease, wherein the endonuclease cleaves the 5' FLAP thereby releasing the 5' FLAP from the second probe oligonucleotide; and (c) instructions for carrying out any of the methods described herein.

In another aspect, this disclosure features compositions including: a first probe oligonucleotide and a second probe oligonucleotide hybridized to an analyte, wherein the first probe oligonucleotide and the second probe oligonucleotide are substantially complementary to adjacent sequences of the analyte, and wherein the second probe oligonucleotide includes a 5' FLAP.

In another aspect, this disclosure features compositions including: a first probe oligonucleotide and a second probe oligonucleotide hybridized to an analyte, wherein the first probe oligonucleotide and the second probe oligonucleotide each include a sequence that is substantially complementary to adjacent sequences of the gDNA molecule; wherein the first probe oligonucleotide and the second probe oligonucleotide are capable of forming an invasive cleavage structure in the presence of the genetic variant; and wherein the second probe oligonucleotide further includes a 5' FLAP. In some embodiments, the 5' FLAP includes a sequence that is capable of hybridizing to a capture domain of a capture probe. In some embodiments, the capture probe further includes a spatial barcode. In some embodiments, the capture probe is part of a plurality of capture probes affixed to a substrate.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
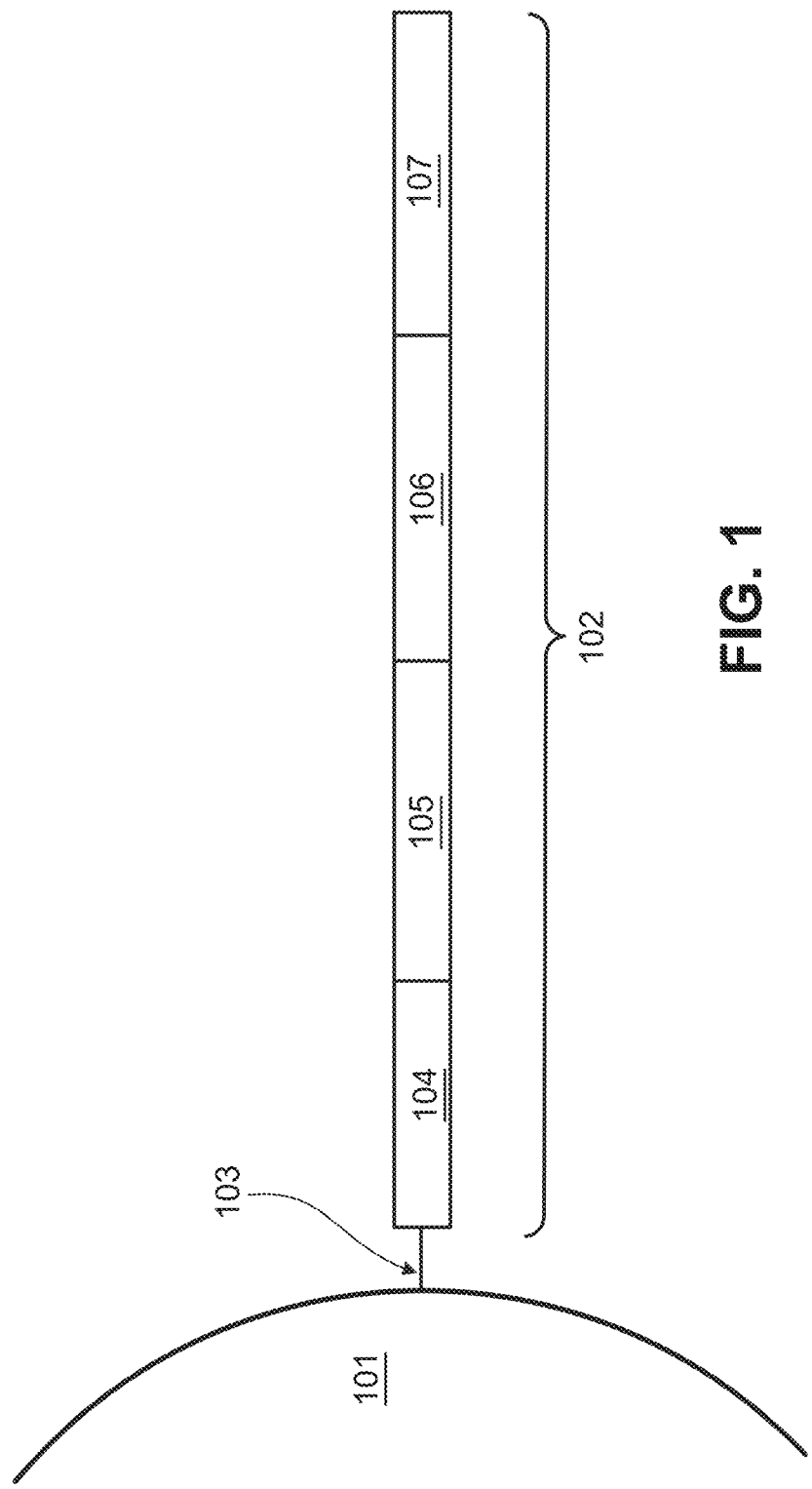
FIG. 1 is a schematic diagram showing an example of a barcoded capture probe, as described herein.

I. Methods and Compositions for Spatial Analysis

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, the capture probe further includes a unique molecular identifier. In some embodiments, the capture probe further includes a functional domain. In some embodiments, the capture domain includes a sequence that is partially complementary to the analyte or an analyte binding moiety. In some embodiments, the capture domain includes a homopolymeric sequence. In some embodiments, the capture domain includes a poly(T) sequence. In some embodiments, the capture probe further includes a cleavage domain. In some embodiments, the cleavage domain includes a cleavable linker. Non-limiting examples of a cleavable linker include a photocleavable linker, a UV-cleavable linker, an enzymatic cleavable linker, or a pH-sensitive cleavable linker. In some embodiments, the plurality of capture probes are attached to one or more features.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a ligation product described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence complementary to a sequence of a nucleic acid analyte, a portion of a ligation product described herein, a capture handle sequence described herein, and/or a methylated adaptor described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
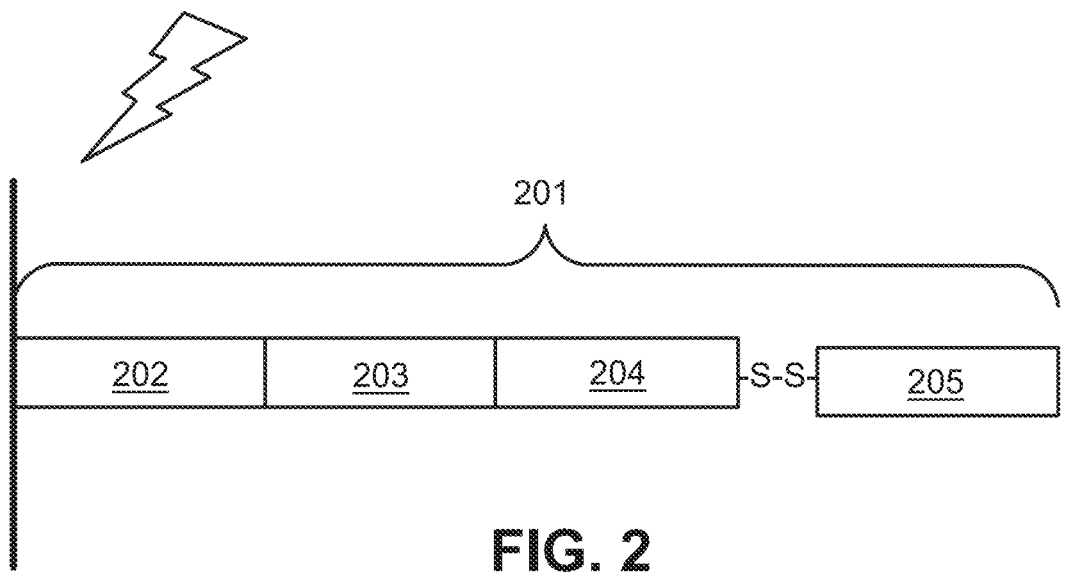
FIG. 2 is a schematic illustrating a cleavable capture probe, wherein the cleaved capture probe can enter into a cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain. Cleavable capture probe are further described in WO 2020/176788 and/or U.S. Patent Application Publication No. 2020/0277663, each of which is incorporated by reference in its entirety.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 3:
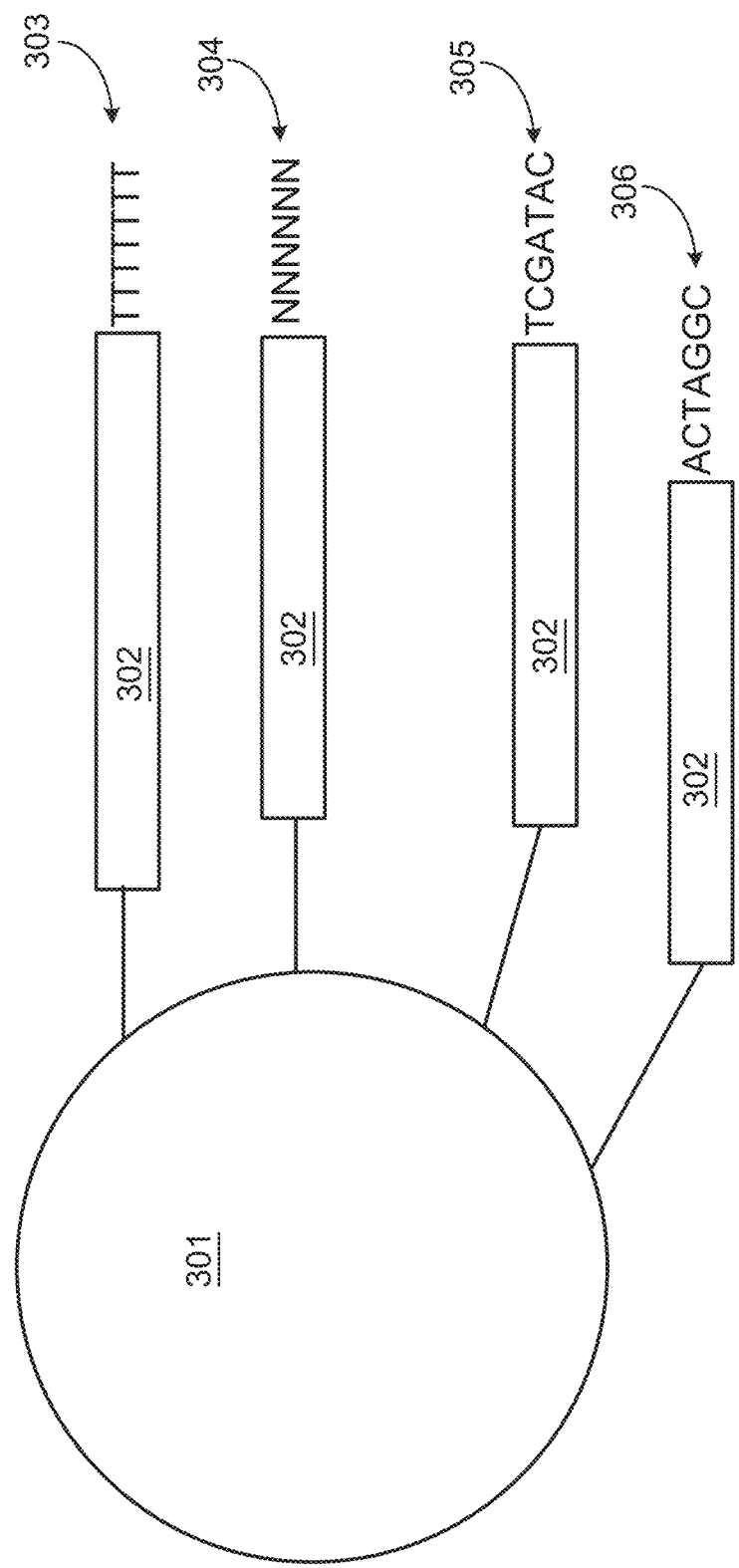
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence or capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Figure 4:
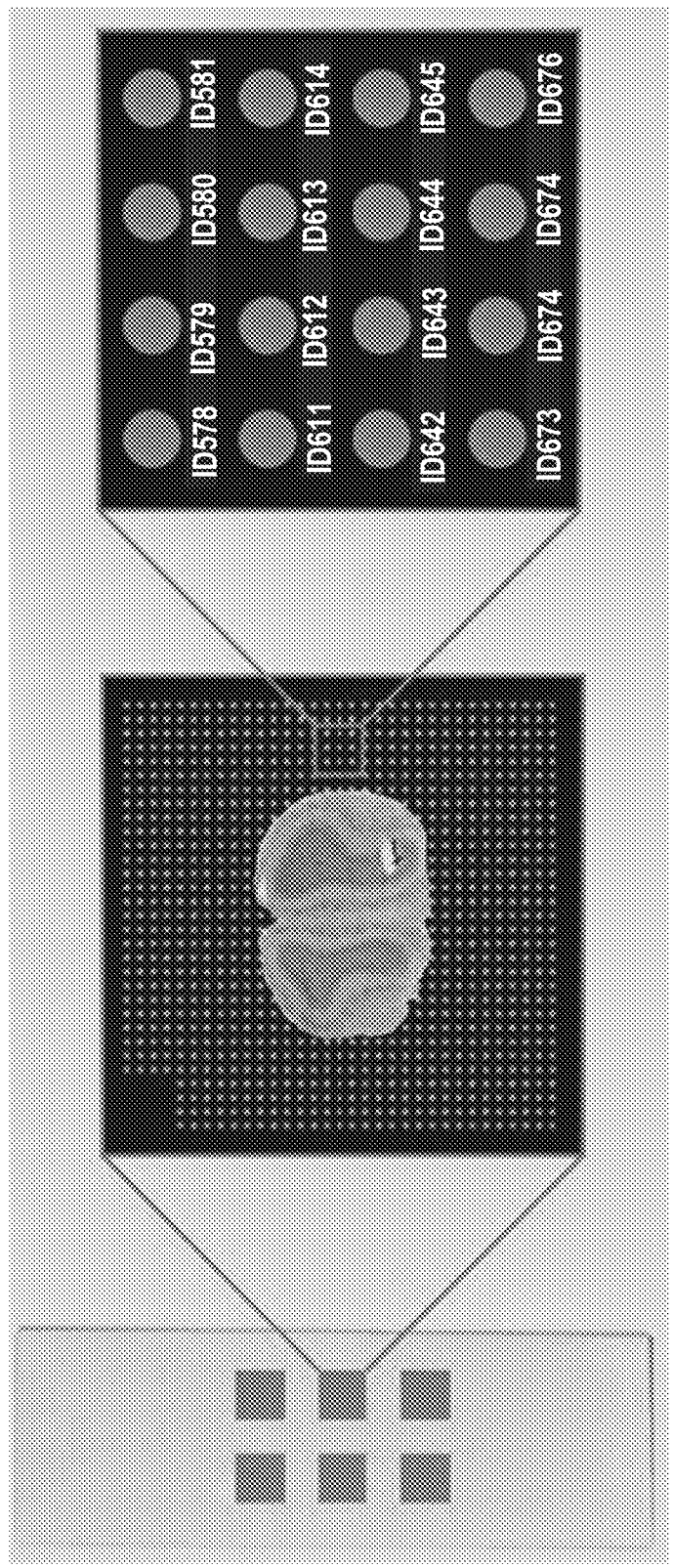
FIG. 4 is a schematic showing the arrangement of barcoded features within an array.

FIG. 4 depicts an exemplary arrangement of barcoded features within an array. From left to right, FIG. 4 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion).

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections *Control Slide for Imaging, Methods of Using Control Slides and Substrates for, Systems of Using Control Slides and Substrates for Imaging*, and/or *Sample and Array Alignment Devices and Methods, Informational labels* of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the *Substrate Attributes* Section, *Control Slide for Imaging* Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distance.

II. Using Barcoded 5' FLAP Probes for the Detection of gDNA (a) DNA-Templated Ligation Using a 5' FLAP Sequence Templated ligation, or RNA templated ligation (RTL), is a process that includes multiple RTL probes (e.g., usually two oligonucleotides or probes) that hybridize to adjacent complementary mRNA sequences. RNA-templated ligation is enabled by the ability of RNases to remove the RNA in a RNA-DNA hybrid. Provided herein are methods that co-opt RTL principles to include oligonucleotide probes that hybridize to adjacent complementary genomic DNA (gDNA) sequences. It is known that DNA-DNA hybrids are harder to separate than RNA-DNA hybrids. Therefore, a readout of the DNA-templated ligation event is needed that can be measured without having to make single stranded DNA from the DNA-DNA hybrid. Here, an oligonucleotide (e.g., a second RTL probe) includes a 5' FLAP sequence that can be removed and detected following an enzyme-mediated cleavage event that does not require removal of the hybridized probes. Detection of the 5' FLAP provides a readout for the DNA-templated ligation event, which can serve as a proxy for detecting a gDNA analyte or a genetic variant within a gDNA analyte.

The methods provided herein rely on the cleavage of the 5' FLAP from the second RTL probe occurring when the first RTL probe and the second RTL probe hybridize to a gDNA analyte at adjacent sequences. In some cases, the adjacent sequences flank a target sequence (e.g., a genetic variant). In some cases, the adjacent sequences directly abut each other in the gDNA analyte. Once a first RTL probe and a second RTL probe hybridize to a gDNA analyte, an enzyme-mediated cleavage event cleaves the second RTL probe, which includes non-complementary nucleotides (e.g., a 5' FLAP). Upon cleavage of the 5' FLAP, the sequence of the 5' FLAP can be determined and used to detect the presence of a gDNA analyte in a biological sample or the presence of a genetic variant in a gDNA analyte. In some instances, determining the sequence of the 5' FLAP includes hybridizing the 5' FLAP to a probe on an array. In such cases, the 5' FLAP includes a capture probe binding domain sequence (e.g., a poly-adenylation sequence or a target nucleic acid sequence) that can be detected by a capture probe on an array described herein (e.g., the capture probe comprises a poly-thymine sequence in some instances). In some instances, determining the sequence of the 5' FLAP includes sequencing the 5' FLAP without first hybridizing the 5' FLAP to a capture probe on an array.

Thus, the methods provided herein allow detection of a gDNA analyte or a genetic variant in a gDNA analyte and in some cases enable detection of the spatial location within a biological sample. In addition, the methods provided herein allow detection of a gDNA analyte within a subset of DNA analytes, thereby increasing the resolution of the technology as applied to gDNA. Also, the methods provided herein avoid the need for probe ligation and endoribonuclease (e.g., RNaseH) treatment, which are both used in a standard RTL workflow, thereby keeping costs low without sacrificing efficiency.

Disclosed herein are methods for detecting an gDNA analyte in a biological sample where (i) the first RTL probe and second RTL probe hybridize to adjacent sequences on the gDNA analyte, (ii) enzyme-mediated cleavage of a 5' FLAP results in release of the 5' FLAP, and (iii) the sequence of the 5' FLAP is determined and used to detect the gDNA in the biological sample. In some embodiments, the method includes detecting a gDNA analyte at a spatial location in a biological sample using a substrate to capture the released 5' FLAP. In such cases, the method includes contacting the biological sample with a substrate that has a plurality of capture probes, where a capture probe of the plurality of capture probes includes a spatial barcode and a capture domain, prior to the RTL probe hybridization step. After cleavage of the 5' FLAP, it hybridizes to the capture domain, and the sequence of the 5' FLAP is determined. The along with determination of the spatial barcode, the spatial location of the gDNA analyte in the biological sample can be detected.

The methods disclosed herein use compositions comprising an RTL probe (e.g., a second RTL probe) that has a non-hybridizing sequence that can be used to carry information about the hybridization event between an analyte and an oligonucleotide. In some instances, the non-hybridizing sequence is referred to as a 5' FLAP. See e.g., FIG. 5, which shows the non-hybridizing 5' FLAP on the Right Hybridizing Sequence (RHS) RTL probe. As disclosed herein, the sequence of the 5' FLAP is used to convey information about a gDNA analyte. For example, described herein are methods were the presence of a 5' FLAP sequence in a sequencing library indicates either the presence or absence of a gDNA analyte or the presence or absence of a genetic variant in an gDNA analyte. In some embodiments, the methods provided herein further include contacting a biological sample that includes the 5' FLAP with a substrate in order to determine the location of the gDNA analyte or genetic variant within the biological sample. In some instances, the 5' FLAP can convey information about a gDNA analyte via other mechanisms including by labeling the 5' FLAP with a detectable label (e.g., any of the exemplary detectable labels described herein) and then detecting the label and using detection of the label as a proxy for the presence or absence of a gDNA analyte or genetic variant in a gDNA analyte.

In some embodiments, the subset of analytes includes gDNA analytes including DNA that is transcribed into RNA (e.g., coding regions including, without limitation, gene exons, gene introns, and untranslated regions (both 5' and 3')) and DNA that is not transcribed into RNA but regulates transcription of DNA into RNA (e.g., regulatory sequences including, without limitation, promoters, enhancers, and silencers). Additional gDNA analytes include gDNA sequences associated with a particular region of a chromosome (e.g., without limitation, a telomere, a centromere, a topologically associated domain, an arm of a chromosome, a portion of an arm of a chromosome, a condensed chromosome, and an uncondensed chromosome).

In some embodiments, the subset of analytes includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, about 1000, or more analytes.

Methods disclosed herein can be performed on any type of sample. In some embodiments, the sample is a fresh tissue. In some embodiments, the sample is a frozen sample. In some embodiments, the sample was previously frozen. In some embodiments, the sample is a formalin-fixed, paraffin embedded (FFPE) sample. FFPE samples generally are heavily cross-linked and fragmented, and therefore this type of sample allows for limited DNA recovery using conventional detection techniques. In certain embodiments, methods of targeted DNA capture provided herein are less affected by DNA degradation associated with FFPE fixation than other methods (e.g., methods that take advantage of oligo-dT capture and reverse transcription of gDNA). In certain embodiments, methods provided herein enable sensitive measurement of specific genes of interest that otherwise might be missed with a whole transcriptomic approach.

In some embodiments, a biological sample (e.g. tissue section) can be fixed with methanol, stained with hematoxylin and eosin, and imaged. In some embodiments, fixing, staining, and imaging occurs before one or more RTL probes are hybridized to the sample. Some embodiments of any of the workflows described herein can further include a destaining step (e.g., a hematoxylin and eosin destaining step), after imaging of the sample and prior to permeabilizing the sample. For example, destaining can be performed by performing one or more (e.g., one, two, three, four, or five) washing steps (e.g., one or more (e.g., one, two, three, four, or five) washing steps performed using a buffer including HCl). The images can be used to map spatial gene expression patterns back to the biological sample. A permeabilization enzyme can be used to permeabilize the biological sample directly on the slide.

In some embodiments, the methods of targeted DNA capture as disclosed herein include hybridization of multiple RTL probes. In some embodiments, the methods include 2, 3, 4, or more RTL probes that hybridize to one or more analytes of interest. In some embodiments, the methods include two RTL probes. In some embodiments, the RTL probe includes sequences complementary that are complementary or substantially complementary to an analyte. For example, in some embodiments, the RTL probe includes a sequence that is complementary or substantially complementary to an analyte (e.g., a gDNA of interest (e.g., to a portion of the sequence of a gDNA of interest)). Methods provided herein may be applied to a single nucleic acid molecule or a plurality of nucleic acid molecules. A method of analyzing a sample comprising a nucleic acid molecule may comprise providing a plurality of nucleic acid molecules (e.g., DNA molecules), where each nucleic acid molecule comprises a first target region (e.g., a sequence that is 3' of a target sequence or a sequence that is 5' of a target sequence) and a second target region (e.g., a sequence that is 5' of a target sequence or a sequence that is 3' of a target sequence), a plurality of first RTL probes, and a plurality of second RTL probes.

After hybridization of the first and second RTL probes, the first RTL probe can be extended. After hybridization, in some embodiments, the second RTL probe can be extended. Extending probes can be accomplished using any method disclosed herein. In some instances, a polymerase (e.g., a DNA polymerase) extends the first and/or second RTL probe.

In some embodiments, methods disclosed herein include a wash step. In some instances, the wash step occurs after hybridizing the first and the second RTL probes. The wash step removes any unbound probes and can be performed using any technique or solution disclosed herein or known in the art. In some embodiments, multiple wash steps are performed to remove unbound RTL probes.

In some embodiments, after hybridization of RTL probes (e.g., first and the second RTL probes) to the gDNA analyte, the 5' FLAP is cleaved, releasing the 5' FLAP. Releasing the 5' FLAP can be performed enzymatically as described herein. As disclosed in the following sections, releasing the 5' FLAP allows for detection of a gDNA analyte of interest.

(i) gDNA Detection in a Biological Sample Using a 5' FLAP

This disclosure features a method for detecting a gDNA analyte in a biological sample using methods that co-opt RTL principles to include RTL probes that hybridize to adjacent complementary genomic DNA (gDNA) sequences.

In particular, the methods disclosed herein utilize a process that cleaves a non-hybridized sequence of one of the RTL probes. The non-hybridized sequence (e.g., a 5' FLAP) can be further analyzed to determine the presence or absence of a gDNA analyte of interest.

A non-limiting example of a method for detecting a gDNA analyte in a biological sample includes: (a) contacting the biological sample with a first RTL probe and a second RTL probe, wherein the first RTL probe and the second RTL probe are substantially complementary to adjacent sequences of the gDNA analyte, and wherein the second RTL probe includes a 5' FLAP; (b) hybridizing the first RTL probe and the second RTL probe to the gDNA analyte; (c) cleaving the second RTL probe, thereby releasing the 5' FLAP; (d) determining all or a part of the sequence of the 5' FLAP, and using the sequence of the 5' FLAP to detect the gDNA analyte. In some embodiments, the method also includes denaturing the gDNA under conditions wherein the first RTL probe and the second RTL probe can hybridize to the gDNA analyte. In some embodiments, the method includes a denaturing step prior to contacting the biological sample with a first RTL probe and a second RTL probe. In some embodiments, the method further includes, prior to (a), contacting the biological sample with a substrate comprising capture probes. In some embodiments, the method further includes contacting the biological sample with a permeabilization reagent. In some embodiments, the biological sample is contacted with the permeabilization reagent before determining all or a part of the sequence of the 5' FLAP, and using the sequence of the 5' FLAP to detect the gDNA analyte. In some embodiments, the method also includes determining step includes amplifying all or part of the 5' FLAP. In some embodiments, the amplifying includes isothermal amplification. In some embodiments, the determining step includes sequencing.

In some embodiments, the cleaving step includes contacting with an endonuclease. The endonuclease can include a 5' FLAP endonuclease activity where the enzyme catalyzes the cleavage of a 5' FLAP structure. The step uses two RTL probes that are hybridized to target nucleic acid (e.g., gDNA) containing, for example, a polymorphic site. One RTL probe is complementary to the target sequence 3' of the polymorphic site and ends with a non-matching base overlapping the SNP nucleotide. The second RTL probe, the allele-specific probe, contains the complementary base of the SNP allele and extends to the sequence 5' of the polymorphic site. This probe can also extend on its 5' site with additional non-complementary nucleotides. An invasive cleavage structure is formed when the first RTL probe and the second RTL probe are both hybridized to the gDNA molecule. Once the two oligonucleotides anneal to the target DNA, they form a three-dimensional invasive structure over the SNP site that can be recognized by cleavase, a FEN enzyme. The enzyme cleaves the probe 3' of the base complementary to the polymorphic site (i.e. 3' of the overlapping invader structure). After hybridization, the invasive cleavage structure is formed when the first RTL probe and the second RTL probe are both hybridized to the gDNA analyte. Additional exemplary support for the invasive cleavage structure utilized in an Invader assay is provided in Olivier, *Mutat. Res.*, 2005 Jun. 3; 573(1-2): 103-110, which is incorporated by reference in its entirety.

In some embodiments, the endonuclease cleaves a portion of the second RTL probe. In some embodiments, the endonuclease cleaves the 5' FLAP of the second RTL probe. Non-limiting examples of endonucleases with 5'-FLAP endonuclease activity that can be used in the cleaving step include DNA replication helicase 2 (DNA2), Exonuclease 1 (EXO1), FANCD2/FANCI-associated nuclease 1 (FAN1), Holliday junction 5' flap endonuclease (GEN1), structure-specific endonuclease subunit homolog B (SLX1B), and GRF-type containing 1 (ZGRF1). In some embodiments, the endonuclease is FLAP endonuclease 1 (FEN1).

In some embodiments, the cleaving step includes providing a DNA-dependent DNA polymerase. The DNA-dependent DNA polymerase can include 3' to 5' exonuclease activity. The DNA polymerase can include strand displacement properties. For example, the DNA polymerase uses the strand displacement property to displace the second RTL probe and an endonuclease cleaves the portion of the second RTL probe not bound (e.g., the 5' FLAP and the portion of the second RTL probe displaced by the DNA polymerase) to the target sequence or the sequence 5' of the target sequence. The portion of the second RTL probe not bound to the target sequence or the sequence 5' of the target sequence includes the 5' FLAP. Non-limiting examples of a DNA polymerase that can be used in the cleaving step include Phi29 DNA polymerase and Taq DNA polymerase.

In some embodiments, the 5' FLAP further includes a first barcode sequence. In some embodiments, the first barcode sequence includes a sequence that identifies the first RTL probe, the second RTL probe, and/or the gDNA analyte. In some instances, the first barcode sequence is a sequence unique to the interaction between the first RTL probe, the second RTL probe, and/or the gDNA analyte. Thus, it can be decoded to determine the presence of the interaction between the first RTL probe, the second RTL probe, and/or the gDNA analyte. In some instances, the first barcode sequence can be used to identify the second RTL probe. When the 5' FLAP is cleaved, the 5' FLAP can be used to identify a hybridization event where both the first RTL probe and the second RTL probe hybridize to a gDNA analyte.

In some embodiments, the 5' FLAP also includes a functional sequence. The functional sequence can be a primer sequence. The primer sequence can be used to amplify the 5' FLAP before cleavage, contemporaneously with cleavage, or after cleavage of the 5' FLAP from the second RTL probe.

In some embodiments, the second RTL probe includes a second barcode. For example, the second barcode is on the portion of the second RTL probe that is not released following cleavage. In some embodiments, the second barcode can be used to identify the second RTL probe.

This disclosure features a method for detecting a gDNA analyte at a spatial location in a biological sample using methods that co-opt RTL principles to include RTL probes that hybridize to adjacent complementary genomic DNA (gDNA) sequences. In particular, the methods disclosed herein utilizes a process that cleaves a non-hybridized sequence of an RTL probe. The non-hybridized sequence (e.g., a 5' FLAP) can be further analyzed to determine the presence or absence of a gDNA analyte of interest.

In some instances, a method for detecting a gDNA analyte at a spatial location in a biological sample includes: (a) contacting the biological sample with a substrate including a plurality of capture probes, wherein a capture probe of the plurality includes a spatial barcode and a capture domain; (b) contacting a biological sample with a first RTL probe and a second RTL probe, wherein the first RTL probe and the second RTL probe are substantially complementary to adjacent sequences of the gDNA analyte, and wherein the second RTL probe includes a 5' FLAP; (c) hybridizing the first RTL probe and the second RTL probe to the gDNA analyte; (d) cleaving the second RTL probe, thereby releasing the 5'

FLAP; (e) hybridizing the 5' FLAP to the capture domain; and (f) determining (i) all or a part of the sequence of the 5' FLAP, or a complement thereof, and (ii) all or a part of the sequence of the spatial barcode, or a complement thereof, and using the determined sequence of (i) and (ii) to identify the location of the gDNA analyte in the biological sample. In some embodiments, the method also includes denaturing the gDNA under conditions wherein the first RTL probe and the second RTL probe can hybridize to the gDNA analyte. In some embodiments, the method includes a denaturing step prior to contacting a biological sample with a first RTL probe and a second RTL probe. In some embodiments, the method further includes contacting the biological sample with a permeabilization reagent. In some embodiments, the biological sample is contacted with the permeabilization reagent before contacting the biological sample with a substrate including a plurality of capture probes. In some embodiments where the method includes detecting an analyte at a spatial location in a biological sample, the determining step includes amplifying all or part of the 5' FLAP specifically bound to the capture domain. For example, the amplification can be isothermal. The determining step can include sequencing the 5' FLAP.

In some embodiments, the cleaving step includes providing an endonuclease. The endonuclease can include a 5' FLAP endonuclease activity where the enzyme catalyzes the cleavage of a 5' FLAP structure. In some embodiments, the endonuclease cleaves a portion of second RTL probe. In some embodiments, the endonuclease cleaves the 5' FLAP of the second RTL probe. Non-limiting examples of endonucleases with 5'-FLAP endonuclease activity that can be used in the cleaving step include DNA replication helicase 2 (DNA2), Exonuclease 1 (EXO1), FANCD2/FANCI-associated nuclease 1 (FAN1), Holliday junction 5' flap endonuclease (GEN1), structure-specific endonuclease subunit homolog B (SLX1B), and GRF-type containing 1 (ZGRF1). In some embodiments, the endonuclease is FLAP endonuclease 1 (FEN1).

In some embodiments, the cleaving step includes providing a DNA-dependent DNA polymerase. The DNA-dependent DNA polymerase can include 3' to 5' exonuclease activity. The DNA polymerase can include strand displacement properties. For example, the DNA polymerase uses the strand displacement property to displace the second RTL probe and an endonuclease cleaves the portion of the second RTL probe not bound to the target sequence (e.g., the 5' FLAP and the portion of the second RTL probe displaced by the DNA polymerase) or the sequence 5' of the target sequence. The portion of the second RTL probe not bound to the target sequence or the sequence 5' of the target sequence includes the 5' FLAP. Non-limiting examples of DNA polymerase that can be used in the cleaving step include Phi29 DNA polymerase and Taq DNA polymerase.

In some embodiments, the method also includes providing a capture probe binding domain blocking moiety that interacts with the capture probe binding domain. In some embodiments, the method further includes releasing the capture probe binding domain blocking moiety from the capture probe binding domain prior to contacting the biological sample with the substrate. In some embodiments, the capture probe binding domain blocking moiety includes a poly-uridine sequence, a poly-thymidine sequence, or both. In some embodiments, releasing the capture probe binding domain blocking moiety from the poly(A) sequence includes denaturing the 5' FLAP.

In some embodiments, the method for detecting an analyte at a spatial location in a biological sample includes a second RTL probe having a 5' FLAP that further includes a first barcode sequence. In some embodiments, the first barcode sequence includes a sequence that identifies the first RTL probe, the second RTL probe, and/or the gDNA analyte. In some embodiments, the 5'FLAP further includes a functional sequence. For example, the functional sequence is a primer sequence.

In some embodiments, the 5' FLAP further includes a capture probe binding domain. The capture domain includes a sequence that is substantially complementary to a capture domain on a capture probe where the capture probe binding domain sequence enables binding of the 5' FLAP to the capture probe. The capture probe binding domain can include a homopolymeric sequence. For example, without limitation, the capture probe binding domain can be a poly(A) sequence.

In some embodiments, the method for detecting an analyte at a spatial location in a biological sample includes a second RTL probe that includes from 5' to 3': a 5' FLAP and a sequence that is substantially complementary to a sequence that is adjacent to a sequence that is substantially complementary to a first RTL probe. In other cases, the second RTL probe includes a 5' FLAP including from 5' to 3': a functional sequence, a first barcode, and a capture probe binding domain sequence.

In some embodiments, the second RTL probe further includes a second barcode. In some embodiments, the second barcode sequence includes a sequence that identifies the first RTL probe, the second RTL probe, and/or the gDNA analyte. In some embodiments, the second barcode sequence includes a sequence that identifies the second RTL probe. A second RTL probe can include from 5' to 3': a 5' FLAP, a sequence that is substantially complementary to a sequence that is adjacent to a sequence that is substantially complementary to a first RTL probe, and a second barcode.

In some embodiments, the second RTL probe further includes a second capture probe binding domain. For example, a second RTL probe can include form 5' to 3': a 5' FLAP, a sequence that is substantially complementary to a sequence that is adjacent to a sequence that is substantially complementary to a first RTL probe, a second barcode, and a second capture probe binding domain. The second capture domain can include any of the exemplary capture probe binding domain sequences describe herein. The second capture probe binding domain enables the portion of the second RTL probe that is not cleaved to hybridize to a capture domain on a capture probe.

(b) SNP Detection Using Templated Ligation and Detection of the 5' FLAP

This disclosure also features methods of detecting a SNP using two oligonucleotide probes that are hybridized to a gDNA analyte containing a polymorphic site. The two oligonucleotides hybridize to the single-stranded target and form an overlapping invader structure at the site of the SNP. One oligonucleotide (e.g., a first RTL probe) is complementary to the target sequence 3' of the polymorphic site and ends with a non-matching base overlapping the SNP nucleotide. The second oligonucleotide (e.g., the second RTL probe), the allele-specific probe, contains the complementary base of the SNP allele and extends to the sequence 5' of the polymorphic site. In some instances, this second oligonucleotide can also include a 5' FLAP including additional non-complementary nucleotides (e.g., a functional sequence and a barcode sequence). Once the two oligonucleotides hybridize to the target DNA, they form a three-dimensional invader structure over the SNP site that can be recognized by a cleavase, such as a FEN enzyme. An invasive cleavage structure is described in U.S. Pat. No. 6,913,881 B1, which is incorporated by reference in its entirety. The enzyme cleaves the 5' FLAP (e.g., the non-complementary nucleotides) of the second RTL probe. Once cleaved, 5' FLAP is released. Additional exemplary support for the invasive cleavage structure utilized in an Invader assay is provided in Olivier, *Mutat. Res.* 2005 Jun. 3; 573(1-2): 103-110, which is incorporated by reference in its entirety. In an alternative embodiment, the cleaved 5' FLAP can be detected using a FRET pair, wherein the release of the FLAP results in fluorescence detection. In some instances, the 5' FLAP includes a tag (e.g., a fluorescent tag) that can be detected upon cleavage. In another embodiment, after cleavage, the supernatant can be extracted and sequencing, providing the ability to detect the presence of a SNP or mutation of interest.

In some embodiments, a method for detecting a gDNA analyte in a biological sample includes (i) hybridizing a first RTL probe and a second RTL probe to adjacent sequences on the gDNA analyte, (ii) cleaving a 5' FLAP from the second RTL probe, thereby releasing the 5' FLAP, and (iii) determining the sequence of the 5' FLAP and using the sequence of the 5' FLAP to detect a genetic variant in the gDNA in the biological sample. In some embodiments, the method includes detecting a gDNA analyte at a spatial location in a biological sample using a substrate to capture the released 5' FLAP. In such cases, the method further includes contacting the biological sample with a substrate including a plurality of capture probes, wherein, a capture probe of the plurality includes a spatial barcode and a capture domain, hybridizing the 5' FLAP to the capture domain, and determining the sequence of the 5' FLAP and using the sequence of the 5' FLAP to detect a genetic variant in a gDNA analyte at a spatial location in the biological sample.

In some embodiments, a method of detecting a genetic variant in a gDNA analyte in a biological sample includes determining all or a part of the sequence of the 5' FLAP, and using the sequence of the 5' FLAP to detect the genetic variant in the gDNA analyte without using a substrate including capture probes to capture the 5' FLAP. In such cases, the 5' FLAP does not include a capture probe binding domain sequence. In such cases, a gDNA analyte is contacted with a first RTL probe and a second RTL probe, wherein the first RTL probe and the second RTL probe each include a sequence that is substantially complementary to adjacent sequences of the gDNA analyte; wherein the first RTL probe and the second RTL probe are capable of forming an invasive cleavage structure in the presence of the genetic variant; and wherein the second RTL probe further includes a 5' FLAP. The 5' FLAP can include a barcode sequence that can be used to identify the first RTL probe, the second RTL probe, and/or the gDNA analyte. In some cases, the method also includes denaturing the gDNA under conditions wherein the first RTL probe and the second RTL probe can hybridize to the gDNA analyte. The first RTL probe and the second RTL probe can hybridize to the gDNA analyte. Following hybridization in the presence of the genetic variant, the second RTL probe can be cleaved, thereby releasing the 5' FLAP. Finally, all or a part of the sequence of the 5' FLAP is determined, and used to detect the genetic variant in the gDNA analyte.

In another embodiment, this disclosure features a method of detecting a genetic variant in a gDNA analyte at a spatial location in a biological sample. In a non-limiting example this method includes contacting the biological sample with a first RTL probe and a second RTL probe, wherein the first RTL probe and the second RTL probe each include a sequence that is substantially complementary to adjacent sequences of the gDNA analyte; wherein the first RTL probe and the second RTL probe are capable of forming an invasive cleavage structure when the genetic variant is present; and wherein the second RTL probe further includes a 5' FLAP. The 5' FLAP can include a barcode sequence that can be used to identify the first RTL probe, the second RTL probe, and/or the gDNA analyte and a capture probe binding domain sequence that can be used to hybridize the 5' FLAP to capture domain of a capture probe located on the surface of a substrate. In some cases, the method also includes denaturing the gDNA under conditions wherein the first RTL probe and the second RTL probe can hybridize to the gDNA analyte. Following hybridization of the first RTL probe and the second RTL probe in the presence of the genetic variant, the second RTL probe can be cleaved, thereby releasing the 5' FLAP. The method then includes contacting the biological sample with a substrate including a plurality of capture probes, wherein a capture probe of the plurality includes a spatial barcode and a capture domain; hybridizing the 5' FLAP to the capture domain; and determining (i) all or a part of the sequence of the 5' FLAP, or a complement thereof, and (ii) all or a part of the sequence of the spatial barcode, or a complement thereof, and using the determined sequence of (i) and (ii) to identify the genetic variant in the gDNA analyte at a spatial location in the biological sample.

In some embodiments, the first RTL probe includes a sequence that is substantially complementary to a sequence 3' of the target sequence (e.g., the genetic variant). In some embodiments, the first RTL probe is at least 70% identical (e.g., at least 75% identical, at least 80% identical, at least 85% identical, at least 90% identical, at least 95% identical, or at least 99% identical) to a sequence 3' of the target sequence (e.g., the genetic variant).

In some embodiments, the first RTL probe includes a sequence that is substantially complementary to a sequence 5' of the target sequence (e.g., the genetic variant). In some embodiments, the first RTL probe is at least 70% identical (e.g., at least 75% identical, at least 80% identical, at least 85% identical, at least 90% identical, at least 95% identical, or at least 99% identical) to a sequence 5' of the target sequence (e.g., the genetic variant).

In some embodiments, the first RTL probe includes at least one nucleotide that is complementary to a reference target sequence (e.g., wild type sequence of a genetic variant). In some embodiments, the first RTL probe includes at least one nucleotide that is complementary to a single nucleotide polymorphism (e.g., a single nucleotide polymorphism as compared to a reference target sequence).

In some embodiments, the second RTL probe includes a sequence substantially complementary to a sequence 5' to the target sequence (e.g., the genetic variant). In some embodiments, the second RTL probe is at least 70% identical (e.g., at least 75% identical, at least 80% identical, at least 85% identical, at least 90% identical, at least 95% identical, or at least 99% identical) to a sequence 5' of the target sequence (e.g., the genetic variant).

In some embodiments, the second RTL probe includes a sequence substantially complementary to a sequence 3' to the target sequence (e.g., the genetic variant). In some embodiments, the second RTL probe is at least 70% identical (e.g., at least 75% identical, at least 80% identical, at least 85% identical, at least 90% identical, at least 95% identical, or at least 99% identical) to a sequence 3' of the target sequence (e.g., the genetic variant).

In some embodiments, the second RTL probe includes at least one nucleotide complementary to the at least one genetic variant of the target sequence. In some embodiments, the second RTL probe includes at least one nucleotide complementary to a reference target sequence (e.g., a wild type sequence).

In some embodiments, the second RTL probe includes from 5' to 3': a sequence of non-complementary nucleotides (e.g., a 5' FLAP), one or more nucleotides complementary to the target sequence (e.g., the genetic variant), and a sequence substantially complementary to a sequence 5' of the target sequence (e.g., the genetic variant). In such cases, the 5' FLAP includes a barcode sequence. Where the 5' FLAP sequence is determined without hybridizing the 5' FLAP to a capture probe, the 5' FLAP does not include a capture probe binding domain sequence. In some cases where the 5' FLAP sequence is determined without hybridizing the 5' FLAP to a capture probe, the 5' FLAP includes a capture probe binding domain sequence. In cases where the sequence of the 5' FLAP is determined by hybridizing the 5' FLAP to a capture probe (i.e., via a capture domain), the 5' FLAP includes a capture probe binding domain sequence.

In some embodiments, the target sequence in an analyte of interest includes one or more nucleotides. In some embodiments, the target sequence includes one or more single nucleotide variants (SNV) compared to a reference target sequence. In some instances, the target sequence includes one SNV compared to a reference target sequence. In some embodiments, the at least one genetic variant is a single nucleotide polymorphism (SNP). For example, a gDNA analyte can include one or more SNPs compared to a reference gDNA analyte. In some embodiments, the at least one genetic variant is a nucleotide point mutation. In some embodiments, the at least one genetic variant includes at least two, at least three, at least four, at least five, or more genetic variants.

In some embodiments, after formation of the invader structure, the biological sample is contacted with an endonuclease. In some instances, the endonuclease cleaves the sequence of non-complementary nucleotides (e.g. a 5' FLAP) of the second RTL probe. In some embodiments, the endonuclease cleaves a portion of the first RTL probe. In some embodiments, the endonuclease is FLAP endonuclease 1 (FEN1). FEN1 is a structure-specific endonuclease that cuts at the base of single-stranded FLAPs. See Balakrishnan and Bambara, *Annu Rev Biochem*. 2013 Jun. 2; 82: 119-138, which is incorporated by reference in its entirety. In some embodiments, the endonuclease cleaves the at least one nucleotide that is complementary to a wild-type sequence of the target sequence of the first RTL probe.

In some instances, once FEN1 cleaves the 5' FLAP, the hybridized RTL probes are ligated using methods disclosed herein (e.g., enzymatically using e.g., T4 DNA ligase or chemically). In some instances, the ligation step comprises ligating the first RTL probe and the 3' end of a gap RTL probe using enzymatic or chemical ligation. In some instances, the ligation step comprises ligating the second RTL probe and the 5' end of a gap RTL probe using enzymatic or chemical ligation. In some instances, the enzymatic ligation utilizes a ligase. In some instances, the ligase is one or more of a T4 DNA ligase (Rnl2), a SplintR ligase, a single stranded DNA ligase, or a T4 DNA ligase. In some instances, the ligase is a T4 DNA ligase 2 (Rnl2) ligase. In some instances, the ligase is a pre-activated T4 DNA ligase. In some embodiments, after releasing the 5' FLAP from the second RTL probe, the biological sample is permeabilized. In some embodiments, permeabilization occurs using a protease (e.g., an endopeptidase disclosed herein).

SNP Detection in a Biological Sample Using a 5' FLAP

This disclosure also features a method of detecting a genetic variant in gDNA analyte in a biological sample where the method includes determining all or a part of the sequence of the 5' FLAP, and using the sequence of the 5' FLAP to detect the genetic variant in the gDNA analyte without using a substrate including capture probes to capture the 5' FLAP.

In another aspect, this disclosure features a method of detecting a genetic variant in a gDNA analyte in a biological sample including: (a) contacting the gDNA analyte with a first RTL probe and a second RTL probe, wherein the first RTL probe and the second RTL probe each include a sequence that is substantially complementary to adjacent sequences of the gDNA analyte; wherein the first RTL probe and the second RTL probe are capable of forming an invasive cleavage structure in the presence of the genetic variant; and wherein the second RTL probe further includes a 5' FLAP; (b) hybridizing the first RTL probe and the second RTL probe to the gDNA analyte; (c) cleaving the second RTL probe when the genetic variant is present, thereby releasing the 5' FLAP; and (d) determining all or a part of the sequence of the 5' FLAP, and using the sequence of the 5' FLAP to detect the genetic variant in the gDNA analyte. In some embodiments, the method also includes denaturing the gDNA under conditions wherein the first RTL probe and the second RTL probe can hybridize to the gDNA analyte. In some embodiments, the method includes a denaturing step prior to contacting the gDNA analyte with a first RTL probe and a second RTL probe. In some embodiments, the method further includes contacting the biological sample with a permeabilization reagent. In some embodiments, the biological sample is contacted with the permeabilization reagent determining all or a part of the sequence of the 5' FLAP, and using the sequence of the 5' FLAP to detect the genetic variant in the gDNA analyte. In some embodiments, the method also includes a determining step including amplifying all or part of the 5' FLAP. In some embodiments, the amplifying includes isothermal amplification. In some embodiments, the determining step includes sequencing.

In some embodiments, the cleaving step includes providing an endonuclease. In some embodiments, the endonuclease cleaves the invasive cleavage structure. In some embodiments, the endonuclease cleaves a portion of the first RTL probe. In some embodiments, the endonuclease cleaves the at least one nucleotide that is complementary to a wild-type sequence of the gDNA analyte of the first RTL probe. In some embodiments, the endonuclease cleaves a portion of the second RTL probe. In some embodiments, the endonuclease cleaves the 5' FLAP of the second RTL probe. In some embodiments, the endonuclease is FLAP endonuclease 1 (FEN1).

In some embodiments, the 5' FLAP further includes a first barcode sequence. In some embodiments, the first barcode sequence includes a sequence that identifies the first RTL probe, the second RTL probe, and/or the gDNA analyte. When the 5' FLAP is cleaved, the 5' FLAP can be used to identify a hybridization event where both the first RTL probe and the second RTL probe hybridize to a gDNA analyte.

In some embodiments, the 5' FLAP also includes a functional sequence. The functional sequence can be a primer sequence. The primer sequence can be used to amplify the 5' FLAP before cleavage, contemporaneously with cleavage, or after cleavage of the 5' FLAP from the second RTL probe. The functional sequence can be a sequence for use in sequencing the FLAP.

In some embodiments, when the method comprises cleaving the second RTL probe when the genetic variant is present, the 5' FLAP includes a nucleotide that is complementary to the genetic variant. In some embodiments, following cleavage of the 5' FLAP, the portion of the second RTL probe that is not released includes a nucleotide that is complementary to the genetic variant.

In some embodiments, the second RTL probe includes a second barcode. For example, the second barcode is on the portion of the second RTL probe that is not released following cleavage. In some embodiments, the second barcode can be used to identify the second RTL probe.

This disclosure features methods of detecting a genetic variant in a gDNA analyte at a spatial location in a biological sample using a substrate to capture the released 5' FLAP. In such cases, the method includes contacting the biological sample with a substrate including a plurality of capture probes, where, a capture probe of the plurality includes a spatial barcode and a capture domain, hybridizing the 5' FLAP to the capture domain, and determining the sequence of the 5' FLAP and using the sequence of the 5' FLAP to detect a genetic variant in a gDNA analyte at a spatial location in the biological sample.

A non-limiting example of a method of detecting a genetic variant in a gDNA analyte at a spatial location in a biological sample includes: (a) contacting the biological sample with a first RTL probe and a second RTL probe, wherein the first RTL probe and the second RTL probe each include a sequence that is substantially complementary to adjacent sequences of the gDNA analyte; wherein the first RTL probe and the second RTL probe are capable of forming an invasive cleavage structure when the genetic variant is present; and wherein the second RTL probe further includes a 5' FLAP; (b) hybridizing the first RTL probe and the second RTL probe to the gDNA analyte; (c) cleaving the second RTL probe when the genetic variant is present, thereby releasing the 5' FLAP; (d) contacting the biological sample with a substrate including a plurality of capture probes, wherein a capture probe of the plurality includes a spatial barcode and a capture domain; (e) hybridizing the 5' FLAP to the capture domain; and (f) determining (i) all or a part of the sequence of the 5' FLAP, or a complement thereof, and (ii) all or a part of the sequence of the spatial barcode, or a complement thereof, and using the determined sequence of (i) and (ii) to identify the spatial location of the gDNA analyte in the biological sample. In some embodiments, the method also includes denaturing the gDNA under conditions wherein the first RTL probe and the second RTL probe can hybridize to the gDNA analyte. In some embodiments, the method includes a denaturing step prior to contacting the biological sample with a first RTL probe and a second RTL probe. In some embodiments, the method further includes contacting the biological sample with a permeabilization reagent. In some embodiments, the biological sample is contacted with the permeabilization reagent before determining all or a part of the sequence of the 5' FLAP, and using the sequence of the 5' FLAP to detect the genetic variant in the gDNA analyte.

In some embodiments, the cleaving step includes contacting with an endonuclease. In some embodiments, the endonuclease cleaves the invasive cleavage structure. In some embodiments, the endonuclease cleaves a portion of the first RTL probe. In some embodiments, the endonuclease cleaves the at least one nucleotide that is complementary to a wild-type sequence of the gDNA analyte of the first RTL probe. In some embodiments, the endonuclease cleaves a portion of second RTL probe. In some embodiments, the endonuclease cleaves the 5' FLAP of the second RTL probe. In some embodiments, the endonuclease is FLAP endonuclease 1 (FEN1).

In some embodiments, the method also includes providing a capture probe binding domain blocking moiety that interacts with the capture probe binding domain. In some embodiments, the method further includes releasing the capture probe binding domain blocking moiety from the capture probe binding domain prior to contacting the biological sample with the substrate. In some embodiments, the capture probe binding domain blocking moiety includes a poly-uridine sequence, a poly-thymidine sequence, or both. In some embodiments, releasing the capture probe binding domain blocking moiety from the poly(A) sequence includes denaturing the 5' FLAP.

In some embodiments where the method includes detecting a genetic variant in a gDNA analyte at a spatial location in a biological sample, the determining step includes amplifying all or part of the 5' FLAP specifically bound to the capture domain. For example, the amplification can be isothermal. In some embodiments, the determining step includes sequencing the 5' FLAP.

In some embodiments, the method of detecting a genetic variant in a gDNA analyte at a spatial location in a biological sample includes a second RTL probe having a 5' FLAP that further includes a first barcode sequence. In some embodiments, the first barcode sequence includes a sequence that identifies the first RTL probe, the second RTL probe, and/or the gDNA analyte. In some embodiments, the 5'FLAP further includes a functional sequence. For example, the functional sequence is a primer sequence. In some embodiments, the 5' FLAP further includes a capture probe binding domain. The capture probe binding domain can include a homopolymeric sequence. For example, without limitation, the capture probe binding domain can be a poly(A) sequence.

In some embodiments, following cleavage of the 5' FLAP, the 5' FLAP includes a nucleotide that is complementary to the genetic variant. In some embodiments, following cleavage of the 5' FLAP, the portion of the second RTL probe that is not released by the cleavage includes a nucleotide that is complementary to the genetic variant.

In some embodiments, the method of detecting a genetic variant in an gDNA analyte at a spatial location in a biological sample includes a second RTL probe that includes from 5' to 3': a 5' FLAP and a sequence that is substantially complementary to a sequence that is adjacent to a sequence that is substantially complementary to a first RTL probe.

In some embodiments, the second RTL probe includes a 5' FLAP including from 5' to 3': a functional sequence, a barcode, and a capture probe binding domain sequence. In some embodiments, the 5' FLAP includes from 5' to 3': a functional sequence, a barcode, a capture probe binding domain sequence, and an additional nucleotide. In some embodiments, the additional nucleotide includes a nucleotide that is complementary to the genetic variant. In some embodiments, the additional nucleotide includes a nucleotide that is complementary to the wild type sequence of the genetic variant. In some embodiments, the second RTL probe further includes a nucleotide that is complementary to the genetic variant.

In some embodiments, the second RTL probe further includes a second barcode. In some embodiments, the second barcode sequence includes a sequence that identifies the first RTL probe, the second RTL probe, and/or the gDNA analyte. In some embodiments, the second barcode sequence includes a sequence that identifies the second RTL probe. A second RTL probe can include from 5' to 3': a 5' FLAP, a sequence that is substantially complementary to a sequence that is adjacent to a sequence that is substantially complementary to a first RTL probe, and a second barcode. In some embodiments, the second RTL probe further includes a second capture probe binding domain. For example, a second RTL probe can include from 5' to 3': a 5' FLAP, a sequence that is substantially complementary to a sequence that is adjacent to a sequence that is substantially complementary to a first RTL probe, a second barcode, and a second capture probe binding domain.

(c) Hybridization of 5' FLAP to Capture Domain

In some embodiments, the 5' FLAP includes a capture probe binding domain, which can hybridize to a capture probe (e.g., a capture probe immobilized, directly or indirectly, on a substrate). In some embodiments, methods provided herein include contacting a biological sample with a substrate, where the capture probe is affixed to the substrate (e.g., immobilized to the substrate, directly or indirectly). In some embodiments, the capture probe includes a spatial barcode and a capture domain. In some embodiments, the capture probe binding domain of the 5' FLAP specifically binds to the capture domain. After hybridization of the 5' FLAP to the capture probe, the 5' FLAP is extended at the 3' end to make a copy of the additional components (e.g., the spatial barcode) of the capture probe.

Figure 9A:
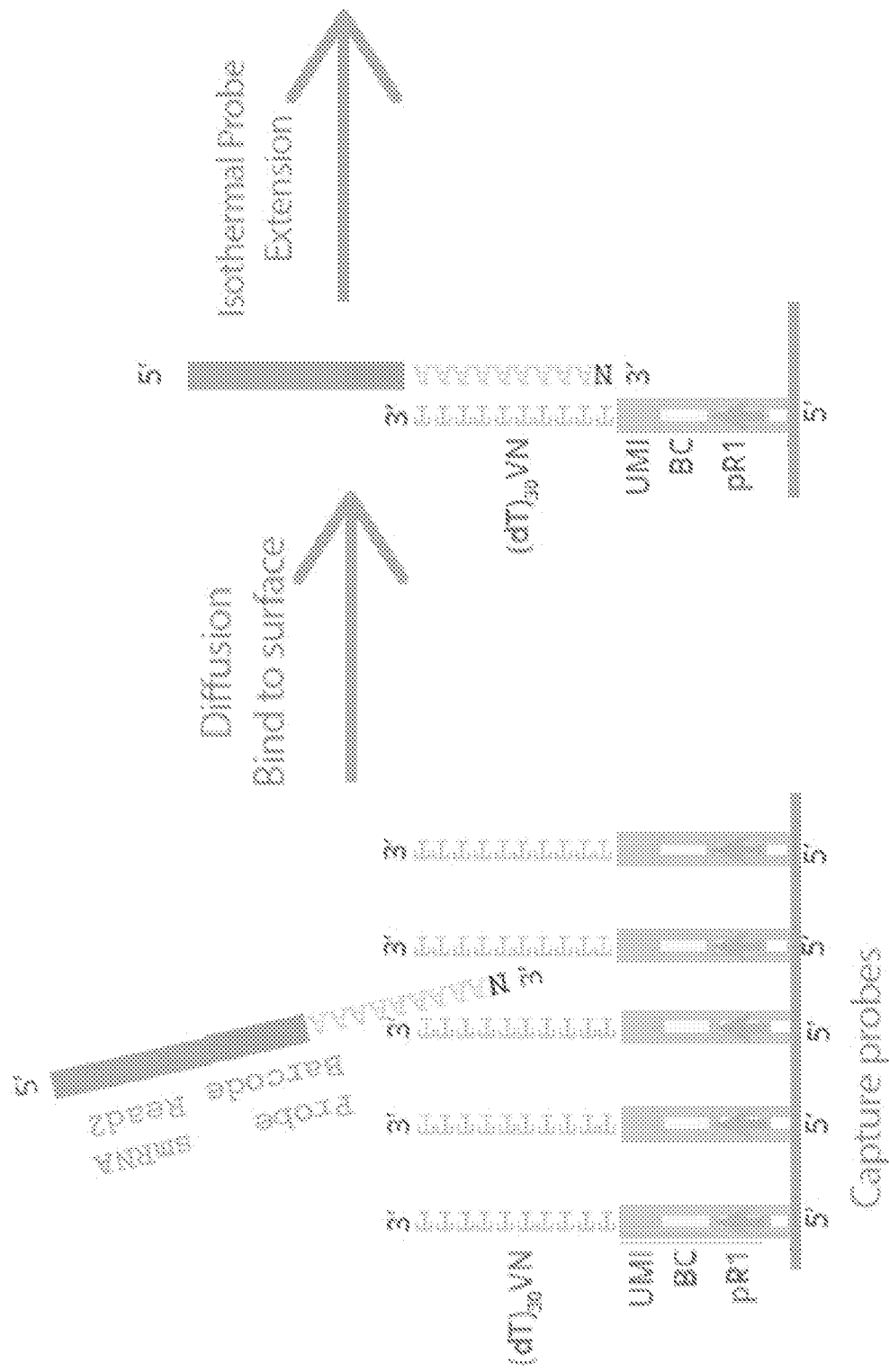
FIGS. 9A and 9B show a schematic of an example workflow where a barcoded 5' FLAP probes is specifically binds to a capture probe on a substrate.
Figure 9B:
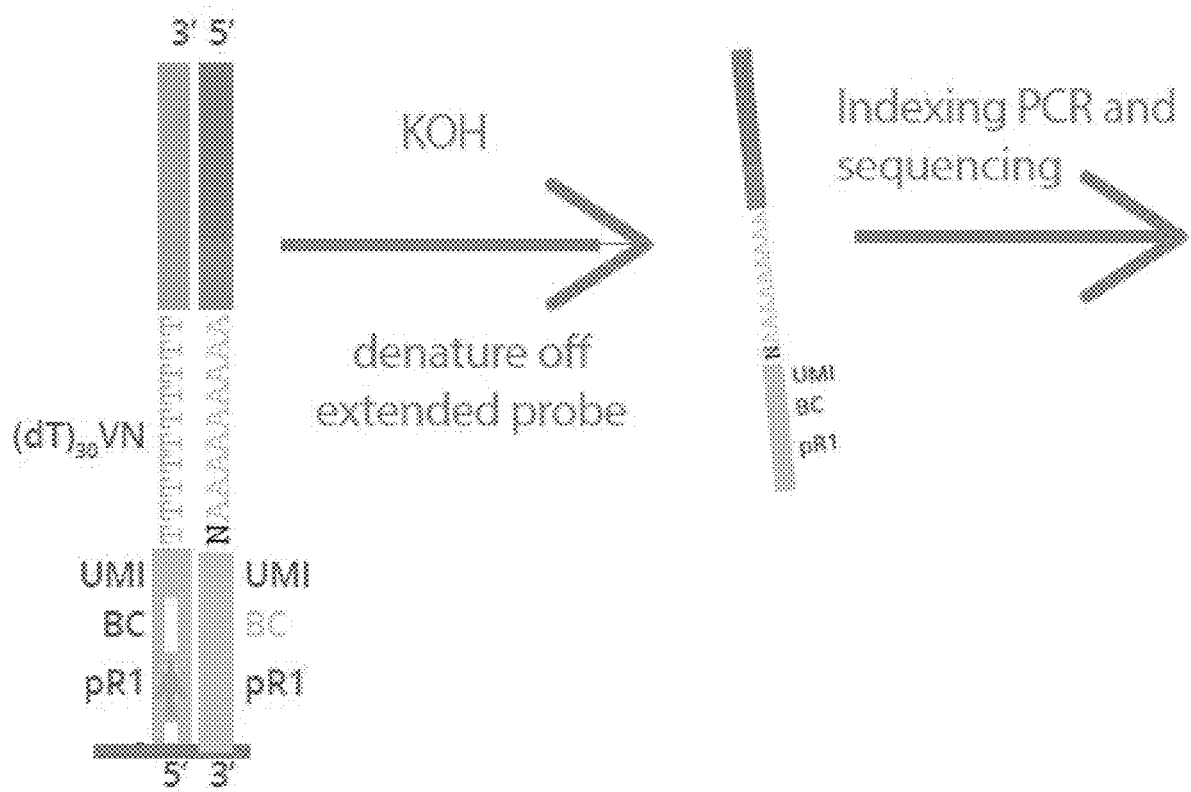

In some embodiments where the 5' FLAP hybridizes to a capture probe on a substrate, the 5' FLAP is extended to generate an extended 5' FLAP. As shown in FIGS. 9A-9B, the 5' FLAP is extended at the 3' end to make a copy of the additional components (e.g., the spatial barcode) of the capture probe. In such cases, the 5' FLAP can include, for example, a sequence complementary to a UMI, spatial barcode, Read 1 sequence (pR1), and a hybridization sequence. In some embodiments, extending the 5' FLAP includes a polymerase enzyme (e.g., a DNA polymerase or DNA polymerase). In some embodiments, the extension reaction can include an isothermal reaction. For example, the extension reaction can use a Phi29 DNA polymerase to extend the 5' FLAP. The Phi29 DNA polymerase includes 3' to 5' exonuclease activity that can be used to remove one or more additional nucleotides from the 3' end of a 5' FLAP. In another example, the extension reaction can use a Bst DNA polymerase to extend the 5' FLAP.

In some embodiments where the 5' FLAP includes an additional nucleotide at the 3' end, extending the 5' FLAP includes using a polymerase having a 3' to 5' exonuclease activity to remove the additional nucleotide sequence from the 3' end and then extend the 5' FLAP. The resulting extended 5' FLAP can be denatured from the capture probe template and transferred (e.g., to a clean tube) for amplification, and/or library construction as described herein. The spatially-barcoded, full-length extended 5' FLAP can be amplified via PCR prior to library construction. P5, P7, i7, and i5 can be incorporated into the library as for downstream sequencing, and additional library sequencing regions, such as TruSeq Read 2, can be added via End Repair, A-tailing, Adaptor Ligation, and PCR. The cDNA fragments can then be sequenced using paired-end sequencing using TruSeq Read 1 and TruSeq Read 2 as sequencing primer sites. In some instances, the cDNA library is sequenced using any method described herein, such that different sequencing domains specific to other sequencing methods and techniques can be incorporated into a capture probe or introduced during library preparation. In some instances, the sequence of the RTL product is determined via sequencing.

In some instances, the spatial barcode is sequenced, providing the location of the gDNA analyte.

(d) RTL Probe Sets Comprising a 5' FLAP on One Probe

Provided herein are templated ligation probes, or RTL probes, that hybridize to adjacent sequences of a target gDNA analyte. Compared to situations of templated ligation where the probes are ligated at each one's terminal end, herein, one of the probes includes a sequence that is not complementary to the target gDNA analyte, and thus overhangs on the side adjacent to the other RTL probes upon RTL probe hybridization.

In some instances, a set of RTL probes comprises a first RTL probe and a second RTL probe. In some instances, the first RTL probe comprises a primer sequence and a sequence complementary to a target analyte (e.g., gDNA). In some instances, the second RTL probe includes a 5' FLAP, a sequence complementary to a target analyte (e.g., gDNA), and a poly(A) sequence. Detailed descriptions of RTL probes has been disclosed in WO 2021/133849, the entirety of which is incorporated herein by reference.

In some embodiments, one of the RTL probes (e.g., the second RTL probe) includes a sequence of non-complementary nucleotides (e.g. a 5' FLAP). In some embodiments, non-complementary nucleotides include ten nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, 50 nucleotides, 51 nucleotides, 52 nucleotides, 53 nucleotides, 54 nucleotides, 55 nucleotides, 56 nucleotides, 57 nucleotides, 58 nucleotides, 59 nucleotides, or at least 60 nucleotides.

In some instances, the 5' FLAP includes a functional sequence. The functional sequence can be a primer sequence. Other non-limiting examples of functional sequences includes Read 1 or Read 2 sequences (e.g., sequences that can be added for sequencing library preparation), index sequences such as an i5 sequence, and/or an i7 sequence (e.g., sequences complementary to P5 and P7), or any other sequence that facilitates detection of the 5' FLAP. In some embodiments, the functional sequence can be a primer sequence where a primer hybridizes to the primer sequence and is used to amplify the 5' FLAP. The 5' FLAP can be amplified using any form of amplification, for example, linear amplification, PCR, of isothermal amplification, and the like.

In some instances, the 5' FLAP includes a barcode sequence. The barcode sequence is a nucleic acid sequence that functions as a label or identifier of the 5' FLAP. The barcode sequence can also function as a label of the first RTL probe, the second RTL probe, and/or the gDNA analyte to which the first RTL probe and the second RTL probe hybridize.

In some instances, the 5' FLAP includes a capture probe binding domain sequence (e.g., any of the exemplary capture probe binding domain sequences described herein). The capture probe binding domain enables the 5' FLAP to hybridize to a capture domain on a capture probe. In some cases, the capture probe is located on the surface of a substrate and includes a spatial barcode and a capture domain. In some embodiments, the capture probe binding domain includes a poly-uridine sequence, a poly-thymidine sequence, or both. In some embodiments, the capture probe binding domain includes a poly(A) sequence. In some embodiments, the capture probe binding domain includes a random sequence (e.g., a random hexamer or octamer). In some embodiments, the capture probe binding domain is complementary to a capture domain in a capture probe that detects a particular target(s) of interest. In some instances, the 5' FLAP does not include a capture probe binding domain sequence. In this instance, identification of the 5' FLAP is performed via downstream analysis (e.g., sequencing the 5' FLAP or a complement thereof without hybridization to a probe on an array).

In some embodiments, the 5' FLAP includes an additional nucleotide on its 3' end. For example, the 5' FLAP includes from 5' to 3': a functional sequence, a barcode, a capture probe binding domain sequence, and an additional nucleotide. The additional nucleotide can include a nucleotide that is complementary to the target sequence (e.g., the genetic variant). Alternatively, the additional nucleotide can include a nucleotide that is complementary to the target sequence (e.g., wild type sequence of the genetic variant). In some embodiments, the 5' FLAP includes an additional two, there, four or five or more nucleotides on its 3' end.

In some embodiments, the subset of analytes includes an individual target DNA. In some instances, the presence of the 5' FLAP that is created as a result of the methods described herein indicates that the individual target DNA is present. In some instances, the absence of the 5' FLAP that is created as a result of the RTL methods described herein indicates that the individual target DNA is present. In some instances, an absence of the 5' FLAP is because one of the RTL probes did not hybridize to the gDNA analyte. In some instances, an absence of the 5' FLAP is because both (e.g., two) of the RTL probes did not hybridize to the gDNA analyte.

In some embodiments, the subset of analytes detected using methods disclosed herein includes two or more (e.g., 2, 3, 4, 5, 6, 7, 8, 9, 10, or more) targeted DNAs. In some instances, the detection of analytes includes detection of one or more mutations in a gDNA analyte. In some embodiments, the subset of analytes includes detection of gDNAs having one or more single nucleotide polymorphisms (SNPs) in a biological sample.

In some embodiments, the methods that allow for targeted DNA capture as provided herein include a first RTL probe and a second RTL probe. The first and second RTL probes each include sequences that are substantially complementary to the sequence of an analyte of interest. By substantially complementary, it is meant that the first and/or second RTL probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in an DNA molecule. In some instances, the first RTL probe and the second RTL probe hybridize to adjacent sequences on a gDNA analyte. It is appreciated that the terms first RTL probe and the second RTL probe generally can be used interchangeably.

In some embodiments, the first and/or second probe as disclosed herein include a combination of ribonucleic acids and deoxyribonucleic acids. In some instances of the first and/or second RTL probes, the sequence that is substantially complementary to the sequence of the analyte of interest includes ribonucleic acids (e.g., does not include deoxyribonucleic acids). In some instances of the first and/or second RTL probes, the sequence that is substantially complementary to the sequence of the analyte of interest includes deoxyribonucleic acids (e.g., does not include ribonucleic acids).

In some embodiments, the first and/or second RTL probe as disclosed herein includes one of at least two ribonucleic acid bases at the 3' end; a functional sequence; a phosphorylated nucleotide at the 5' end; and/or a capture probe binding domain. In some embodiments, the first and/or second RTL probe as disclosed herein includes one of at least two deoxyribonucleic acid bases at the 3' end; a functional sequence; a phosphorylated nucleotide at the 5' end; and/or a capture probe binding domain. In some embodiments, the functional sequence is a primer sequence. The capture probe binding domain is a sequence that is complementary to a particular capture domain present in a capture probe. In some embodiments, the capture probe binding domain includes a poly(A) sequence. In some embodiments, the capture probe binding domain includes a poly-uridine sequence, a poly-thymidine sequence, or both. In some embodiments, the capture probe binding domain includes a random sequence (e.g., a random hexamer or octamer). In some embodiments, the capture probe binding domain is complementary to a capture domain in a capture probe that detects a particular target(s) of interest.

In some embodiments, a capture probe binding domain blocking moiety that interacts with the capture probe binding domain is provided. In some instances, the capture probe binding domain blocking moiety includes a nucleic acid sequence. In some instances, the capture probe binding domain blocking moiety is a DNA oligonucleotide. In some instances, the capture probe binding domain blocking moiety is an RNA oligonucleotide. In some embodiments, a capture probe binding domain blocking moiety includes a sequence that is complementary or substantially complementary to a capture probe binding domain. In some embodiments, a capture probe binding domain blocking moiety prevents the capture probe binding domain from binding the capture probe when present. In some embodiments, a capture probe binding domain blocking moiety is removed prior to binding the capture probe binding domain (e.g., present in a 5' FLAP) to a capture probe. In some embodiments, a capture probe binding domain blocking moiety comprises a poly-uridine sequence, a poly-thymidine sequence, or both.

(e) Biological Samples

Methods disclosed herein can be performed on any type of biological sample, or sample. In some embodiments, the sample is a fresh tissue. In some embodiments, the sample is a frozen sample. In some embodiments, the sample was previously frozen. In some embodiments, the sample is a formalin-fixed, paraffin embedded (FFPE) sample. In certain embodiments, methods provided herein enable sensitive measurement of specific genes of interest that otherwise might be missed with a whole transcriptomic approach.

In some embodiments, a biological sample (e.g. tissue section) can be fixed with methanol, stained with hematoxylin and eosin, and imaged. In some embodiments, fixing, staining, and imaging occurs before one or more oligonucleotide probes are hybridized to the sample. Some embodiments of any of the workflows described herein can further include a destaining step (e.g., a hematoxylin and eosin destaining step), after imaging of the sample and prior to permeabilizing the sample. For example, destaining can be performed by performing one or more (e.g., one, two, three, four, or five) washing steps (e.g., one or more (e.g., one, two, three, four, or five) washing steps performed using a buffer including HCl). The images can be used to map spatial gene expression patterns back to the biological sample. A permeabilization enzyme can be used to permeabilize the biological sample directly on the slide.

(f) Compositions and Kits

In some instances, disclosed herein are compositions and systems that are used to carry out the methods described herein. In some instances, the kit includes a first RTL probe and a second RTL probe. In some instances, the first RTL probe and the second RTL probe in the kit are substantially complementary to adjacent sequences of an analyte. In some instances, the second RTL probe includes a 5' FLAP that is not complementary to the analyte.

In some instances, the kit includes multiple sets of RTL probes, allowing for detection of multiple analytes using one kit. For example, in some instances, the kit includes at least 2 sets, at least 3 sets, at least 4 sets, at least 5 sets, at least 6 sets, at least 7 sets, at least 8 sets, at least 9 sets, or at least 10 sets, or more sets of RTL probes. It is appreciated that multiple sets of probes can detect nucleic acids or variants that are associated with particular physiologies or pathophysiologies (e.g., cancer).

In some instances, the kit includes one or more enzymes, including an endonuclease. In some instances, the endonuclease is FEN1. In some instances, the endonuclease cleaves the 5' FLAP thereby releasing the 5' FLAP from the second RTL probe.

In some instances, the kit further includes a substrate comprising a plurality of capture probes, wherein a capture probe of the plurality comprises a spatial barcode and a capture domain, wherein the 5' FLAP is capable of hybridizing to the capture domain. It is appreciated that the kit can include any of the elements of the substrate, array, or capture probes as described herein.

In some instances, the kit further includes instructions for carrying out the methods of detecting a 5' FLAP as described herein.

In some instances, compositions and systems are further provided herein. In some instances, a composition or system provided herein includes a first RTL probe and a second RTL probe hybridized to an analyte, wherein the first RTL probe and the second RTL probe are substantially complementary to adjacent sequences of the analyte, and wherein the second RTL probe comprises a 5' FLAP. In some instances, a composition or system provided herein includes a first RTL probe and a second RTL probe hybridized to an analyte, wherein the first RTL probe and the second RTL probe each comprise a sequence that is substantially complementary to adjacent sequences of the gDNA analyte; wherein the first RTL probe and the second RTL probe are capable of forming an invasive cleavage structure in the presence of the genetic variant; and wherein the second RTL probe further comprises a 5' FLAP. In some instances, the 5' FLAP comprises a sequence that is capable of hybridizing to a capture domain of a capture probe. In some instances, the capture probe further comprises a spatial barcode. In some instances, the capture probe is part of a plurality of capture probes affixed to any one of the substrates or arrays as described throughout this disclosure.

EXAMPLES

Example 1—Detecting an gDNA Analyte in a Biological Sample Using a 5' FLAP

This example provides an exemplary method of determining the presence or absence of an analyte in a biological sample. In a non-limiting example, a first RTL probe and a second RTL probe are substantially complementary to adjacent sequences of the gDNA analyte, and wherein the second RTL probe includes a 5' FLAP. In the presence of the gDNA analyte in the biological sample, the first and second probes hybridize to the gDNA analyte, the second RTL probe is cleaved thereby releasing the 5' FLAP. The sequence of the 5' FLAP is determined and the determined sequence of the 5' FLAP is used to detect the gDNA analyte.

Figure 5:
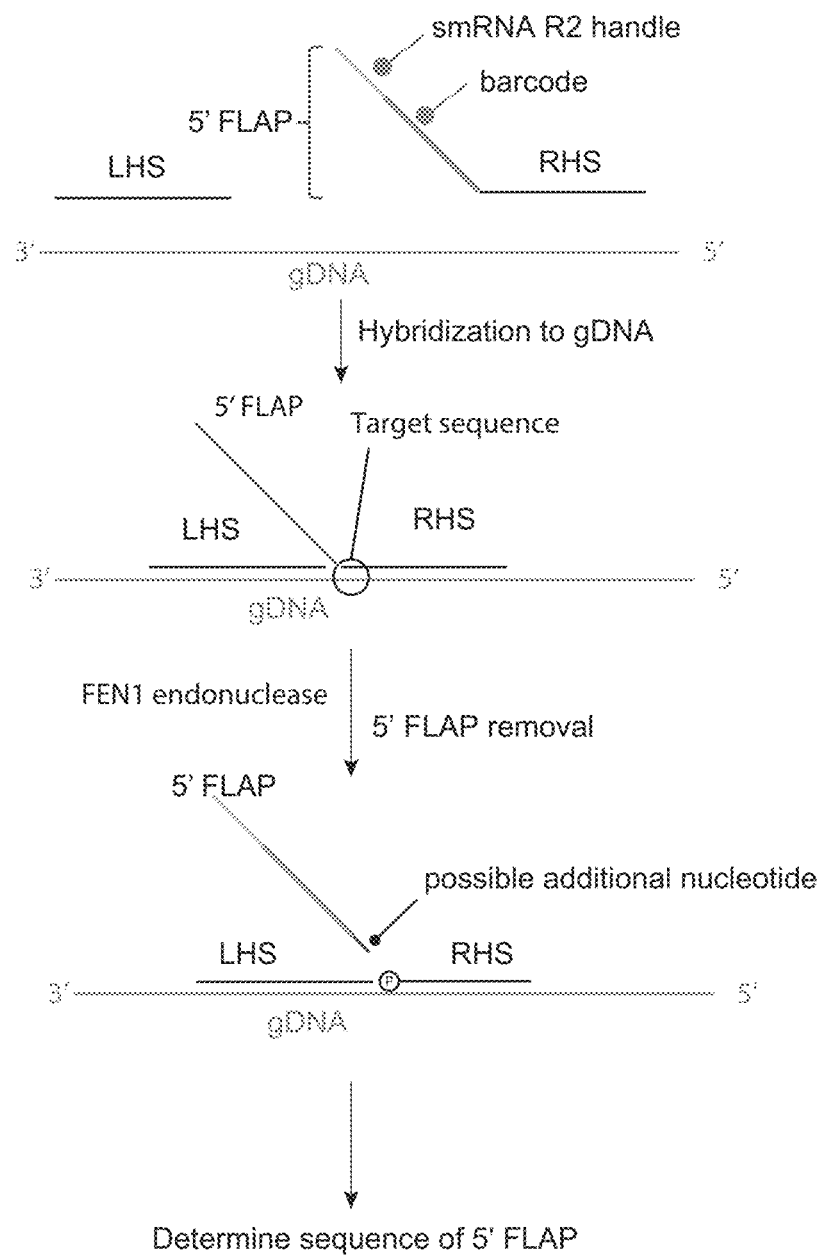
FIG. 5 shows a schematic of an example workflow for using barcoded 5' FLAP probes for the detection of a gDNA analyte. LHS: left hand templated ligation probe; RHS: right hand templated ligation probe; smRNA R2 handle: primer.

As shown in FIG. 5, a gDNA analyte is contacted with a first RTL probe (LHS) and a second RTL probe (RHS). The first RTL probe includes a sequence that is substantially complementary to a sequence that is 3' of a target sequence. The second RTL probe includes a 5' FLAP sequence (e.g., a smRNA R2 handle, and a barcode) and a sequence that is substantially complementary to a sequence that is 5' of the target sequence. Prior to hybridization, the gDNA analyte is denatured under conditions to enable hybridization the RTL probes to the gDNA analyte. The first RTL probe and the second RTL probe can then hybridize to the gDNA analyte. Excess first and second probes are washed off. FEN1 endonuclease cleaves the 5' FLAP thereby removing the 5' FLAP from the second RTL probe. The cleavage occurs when the first RTL probe hybridizes to a sequence that is adjacent to a sequence to which the second RTL probe is hybridized. Following FEN1-mediated cleavage, all or part of the sequence of the 5' FLAP is determined and used to detect a gDNA analyte in a biological sample. Detection can occur via florescence (e.g., FRET pair and release of the FLAP resulting in fluorescence detection).

Example 2—Detecting a Genetic Variant in a gDNA Analyte in a Biological Sample Using a 5' FLAP This example provides an exemplary method for determining the presence or absence of a genetic variant in a gDNA analyte in a biological sample. In a non-limiting example, a first RTL probe having a non-complementary nucleotide overlapping the target sequence (e.g., genetic variant) and a second RTL probe having a sequence complementary to the target sequence (e.g., genetic variant) are used to determine the presence or absence of a genetic variant in a biological sample. Others have demonstrated SNP detection using invader assays. Non-limiting aspects of SNP detection with invader assays are described in U.S. Pat. Nos. 7,011,944, 6,913,881, 6,875,572 and 6,872,816, each of which is incorporated by reference in its entirety and each of which can be used herein in any combination.

Figure 6:
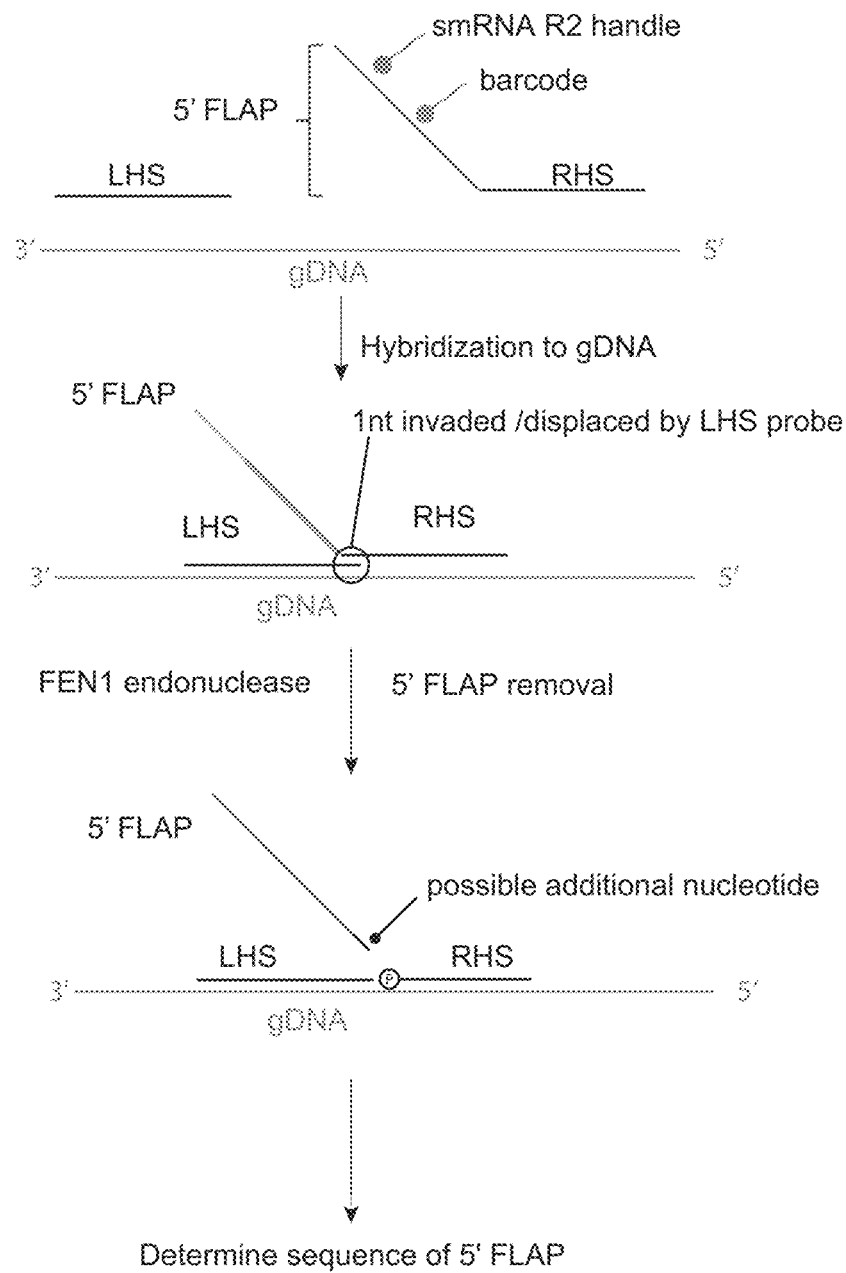
FIG. 6 shows a schematic of an example workflow for using barcoded 5' FLAP probes to detect a genetic variant in a gDNA analyte. 1 nt: one nucleotide.

As shown in FIG. 6, a gDNA analyte that includes a single nucleotide polymorphism (SNP) (i.e., genetic variant) at a target sequence is contacted with a first RTL probe and a second RTL probe. The first RTL probe (LHS) includes a sequence that is substantially complementary to a sequence that is 3' of a target sequence (e.g., genetic variant) and a non-complementary nucleotide that is overlapping the target sequence (e.g., genetic variant). The second RTL probe (RHS) includes a 5' FLAP sequence (e.g., a smRNA R2 handle and a barcode), a nucleotide that is complementary to the target sequence (e.g., genetic variant), and a sequence that is substantially complementary to a sequence 5' of the target sequence (e.g., genetic variant). Prior to hybridization, the gDNA analyte is denatured under conditions to enable hybridization of the RTL probes to the gDNA analyte. The first RTL probe and the second RTL probe can then hybridize to the gDNA analyte. Excess first and second probes are washed off. FEN1 endonuclease cleaves the 5' FLAP thereby removing the non-complementary nucleotides from the second RTL probe. The cleavage occurs when the first RTL probe includes a non-complementary sequence that overlaps with the target sequence (e.g., genetic variant and/or SNP) and the second RTL probe includes a sequence that overlaps with the target sequence and is complementary. In the presence of the genetic variant (e.g., SNP), the first RTL probe and the second RTL probe are then capable of forming an invasive cleavage structure, which is cleaved by FEN1. When the sequence of the second RTL probe is not complementary to the target sequence (e.g., genetic variant) or the first RTL probe includes a complementary sequence that overlaps the target sequence (e.g., genetic variant), no invasive cleavage structure is formed and FEN1-mediated cleave will not occur. Following FEN1-mediated cleavage, all or part of the sequence of the 5' FLAP is sequenced used to determine the presence or absence of a single nucleotide polymorphism (SNP) at the target sequence. Detection can occur via florescence (e.g., FRET pair and release of the FLAP resulting in fluorescence detection).

Example 3—Detecting a gDNA Analyte at a Location in a Biological Sample Using a 5' FLAP and a Substrate This example provides an exemplary method for determining the location of an analyte in a biological sample using a first RTL probe and a second RTL probe.

In a non-limiting example, a first RTL probe and a second RTL probe are substantially complementary to adjacent sequences of the gDNA analyte, and wherein the second RTL probe includes a 5' FLAP. In the presence of the gDNA analyte in the biological sample, the first and second probes hybridize to the gDNA analyte, the second RTL probe is cleaved thereby releasing the 5' FLAP. The sequence of the 5' FLAP is used to detect the gDNA analyte.

Figure 7:
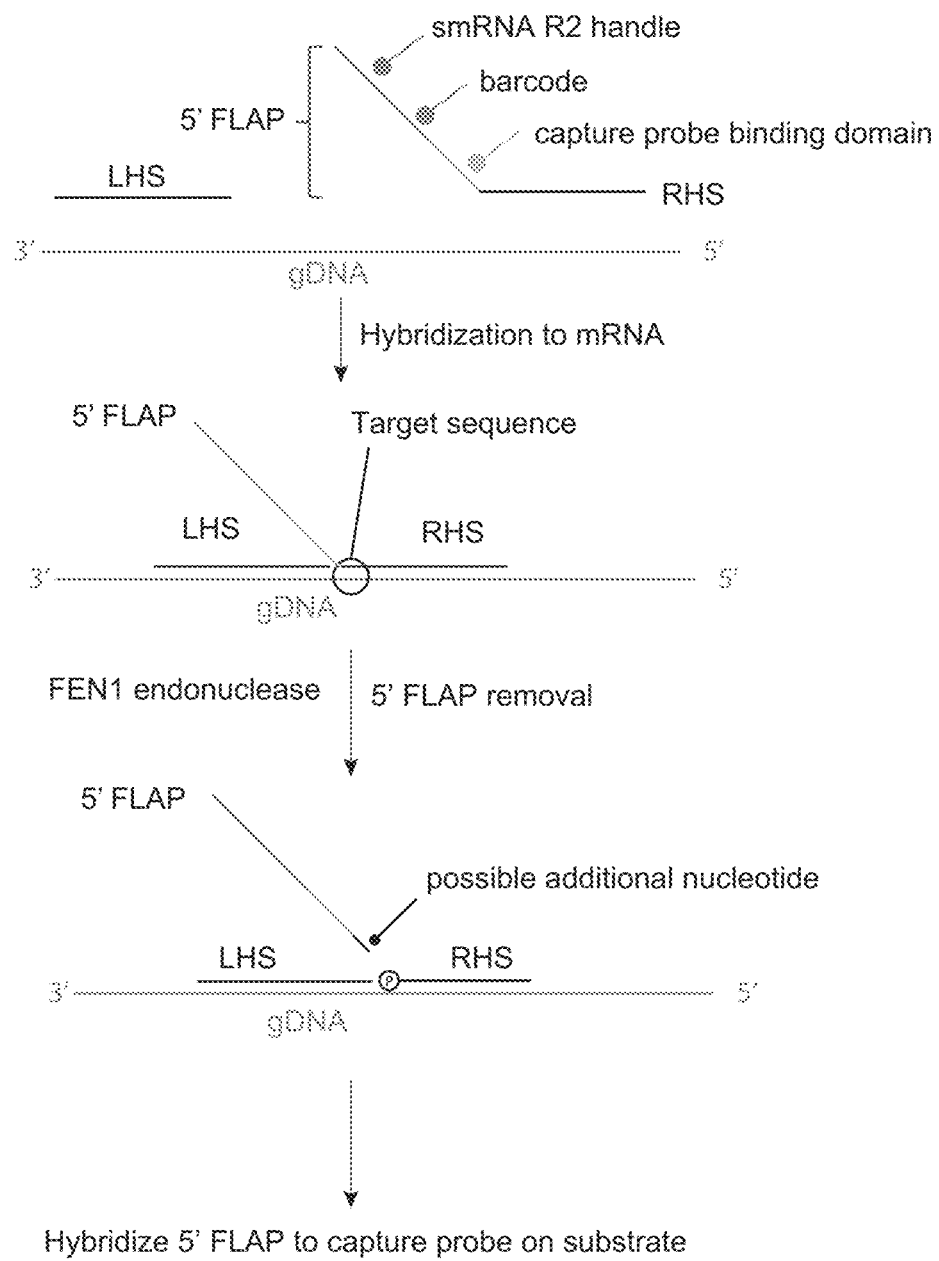
FIG. 7 shows a schematic of an example workflow for using barcoded 5' FLAP probes for detecting a gDNA analyte at a spatial location in a biological sample.

As shown in FIG. 7, a gDNA analyte is contacted with a first RTL probe and a second oligonucleotide. The first RTL probe (LHS) includes a sequence that is substantially complementary to a sequence that is 3' of a target sequence. The second RTL probe (RHS) includes a 5' FLAP sequence (e.g., smRNA R2 handle, barcode, and a capture probe binding domain (e.g., a poly(A) sequence)) and a sequence that is complementary to the target sequence and is substantially complementary to a sequence that is 5' of the target sequence. Prior to hybridization, the gDNA analyte is denatured under conditions to enable hybridization of the RTL probes to the gDNA analyte. The first RTL probe and the second RTL probe can hybridize to the gDNA analyte. Excess first and second probes are washed off. FEN1 endonuclease cleaves the 5' FLAP thereby removing the non-complementary nucleotides from the second RTL probe. The cleavage occurs when the first RTL probe hybridizes to a sequence that is adjacent to the second RTL probe.

As shown in FIGS. 9A-9B, the biological sample is contacted with a substrate that includes capture probes affixed to the substrate, where the capture probes include a spatial barcode and the capture domain. Following cleavage, the capture probe binding domain of the 5' FLAP specifically binds to the capture domain of the capture probe, thereby capturing the 5' FLAP on the substrate. After hybridization of the 5' FLAP to the capture probe, the 5' FLAP is extended at the 3' end to make a copy of the additional components (e.g., the spatial barcode) of the capture probe. Finally, all or part of the sequence of the 5' FLAP specifically bound to the capture domain along with the all or part of the sequence of the spatial barcode of the capture probe is sequenced and used to determine the presence or absence of a single nucleotide polymorphism (SNP) at the target sequence.

Example 4—Detecting a Genetic Variant in a gDNA Analyte at a Location in a Biological Sample Using a 5' FLAP and a Substrate This example provides an exemplary method for determining the presence or absence of a genetic variant in a gDNA analyte in a biological sample. In a non-limiting example, a first RTL probe having a non-complementary nucleotide overlapping the target sequence (e.g., genetic variant) and a second RTL probe having a sequence complementary to the target sequence (e.g., genetic variant) are used to determine the location of a genetic variant in a biological sample.

Figure 8:
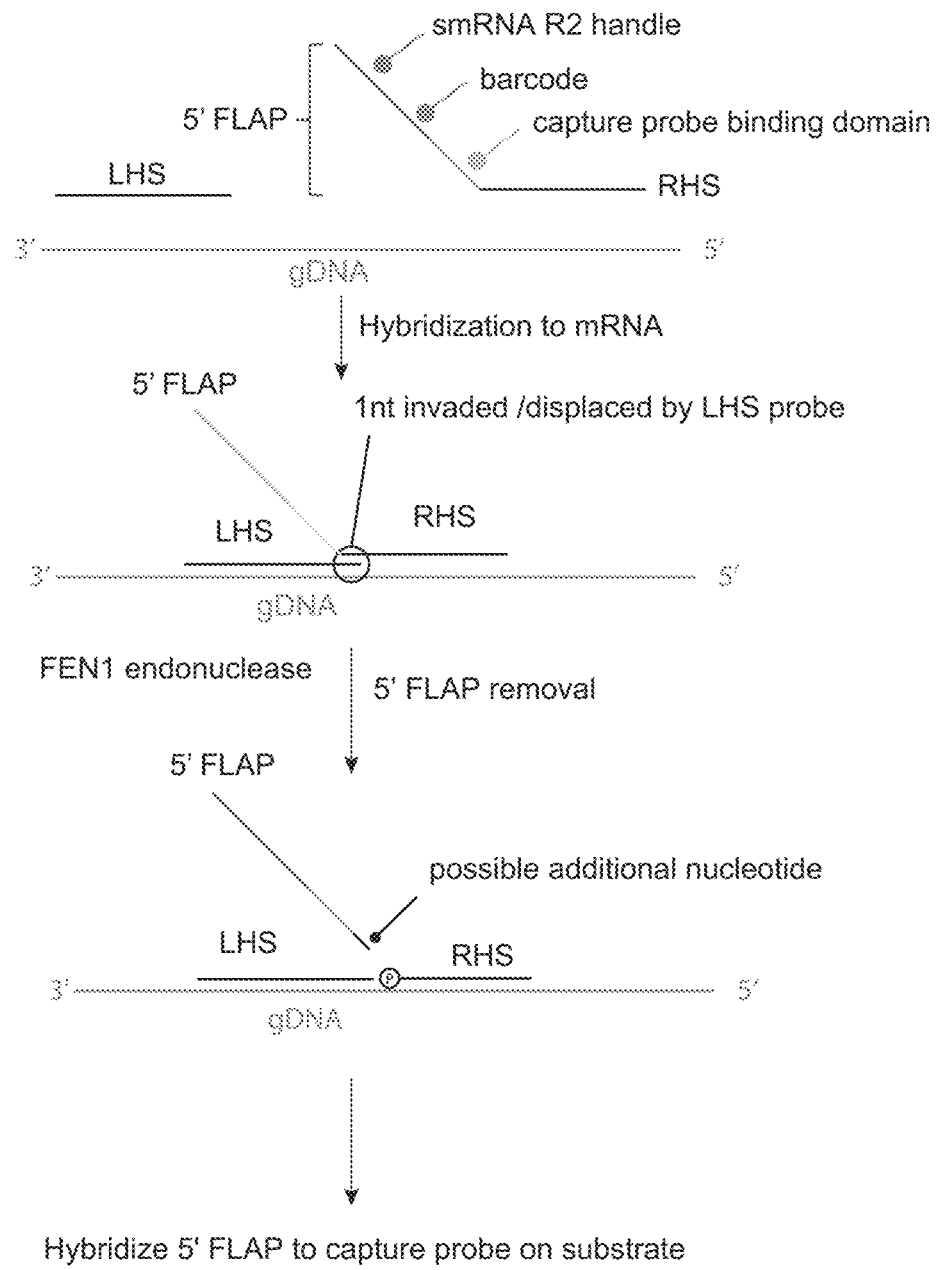
FIG. 8 shows a schematic of an example workflow for using barcoded 5' FLAP probes for detecting a genetic variant in a gDNA analyte at a spatial location in a biological sample

As shown in FIG. 8, a gDNA analyte that includes a single nucleotide polymorphism (SNP) (i.e., genetic variant) at a target sequence is contacted with a first RTL probe and a second RTL probe. The first RTL probe (LHS) includes a sequence that is substantially complementary to a sequence that is 3' of a target sequence (e.g., genetic variant) and a non-complementary nucleotide that is overlapping the target sequence (e.g., genetic variant). The second RTL probe (RHS) includes a 5' FLAP sequence (e.g., smRNA R2 handle, barcode, and a capture probe binding domain (e.g., a poly(A) sequence)), a nucleotide that is complementary to the target sequence (e.g., genetic variant), and a sequence that is substantially complementary to a sequence 5' of the target sequence (e.g., genetic variant). Prior to hybridization, the gDNA analyte is denatured under conditions to enable hybridization of the RTL probes to the gDNA analyte. The first RTL probe and the second RTL probe can hybridize to the gDNA analyte. Excess first and second probes are washed off. FEN1 endonuclease cleaves the 5' FLAP thereby removing the non-complementary nucleotides from the second RTL probe. The cleavage occurs when the first RTL probe includes a non-complementary sequence that overlaps with the target sequence (e.g., genetic variant and/or SNP) and the second RTL probe includes a sequence that overlaps with the target sequence and is complementary. In the presence of the genetic variant (e.g., SNP), the first RTL probe and the second RTL probe are then capable of forming an invasive cleavage structure, which is cleaved by FEN1. When the sequence of the second RTL probe is not complementary to the target sequence (e.g., genetic variant) or the first RTL probe includes a complementary sequence that overlaps the target sequence (e.g., genetic variant), no invasive cleavage structure is formed and FEN1-mediated cleave will not occur.

As shown in FIGS. 9A-9B, the biological sample is contacted with a substrate that includes capture probes affixed to the substrate, where the capture probes include a spatial barcode and the capture domain. Following cleavage, the capture probe binding domain of the 5' FLAP specifically binds to the capture domain of the capture probe, thereby capturing the 5' FLAP on the substrate. After hybridization of the 5' FLAP to the capture probe, the 5' FLAP is extended at the 3' end to make a copy of the additional components (e.g., the spatial barcode) of the capture probe. Finally, all or part of the sequence of the 5' FLAP specifically bound to the capture domain along with the all or part of the sequence of the spatial barcode of the capture probe is sequenced and used to determine the presence or absence of a single nucleotide polymorphism (SNP) at the target sequence.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. In case of conflict, the present specification, including definitions, will control. In addition, section headings, the materials, methods, and examples are illustrative only and not intended to be limiting.

What is claimed is:

1. A method for determining a location of a genomic DNA (gDNA) analyte in a biological sample, the method comprising:
   (a) contacting the biological sample with a substrate comprising a plurality of capture probes, wherein a capture probe of the plurality comprises a spatial barcode and a capture domain;
   (b) contacting the biological sample with a first probe and a second probe, wherein the first probe and the second probe are substantially complementary to adjacent sequences of the gDNA analyte, and wherein the second probe comprises a 5' FLAP;
   (c) hybridizing the first probe and the second probe to the gDNA analyte;
   (d) cleaving the second probe, thereby releasing the 5' FLAP;
   (e) hybridizing the 5' FLAP to the capture domain; and
   (f) determining (i) all or a part of the sequence of the 5' FLAP, or a complement thereof, and (ii) the sequence of the spatial barcode, or a complement thereof, and using the determined sequence of (i) and (ii) to identify the location of the gDNA analyte in the biological sample.

2. The method of claim 1, wherein the first probe and the second probe are DNA probes.

3. The method of claim 1, wherein the 5' FLAP comprises a first barcode sequence, wherein the first barcode sequence comprises a sequence that identifies the first probe, the second probe, the gDNA analyte, or any combination thereof.

4. The method of claim 1, wherein the 5' FLAP comprises (i) a functional sequence, wherein the functional sequence is a primer sequence, and (ii) a capture probe binding domain, wherein the capture probe binding domain comprises a homopolymeric sequence, optionally a poly(A) sequence.

5. The method of claim 1, wherein the cleaving the second probe comprises providing an endonuclease, wherein the endonuclease cleaves a portion of the first probe, a portion of second probe, the 5' FLAP of the second probe, or any combination thereof.

6. The method of claim 5, wherein the endonuclease cleaves the 5' FLAP of the second probe.

7. The method of claim 6, wherein the endonuclease is FLAP endonuclease 1 (FEN1).

8. The method of claim 1, wherein the determining step comprises sequencing all or part of the 5' FLAP.

9. The method of claim 1, wherein the biological sample is a formalin-fixed, paraffin-embedded (FFPE) sample.

10. A kit comprising:
    (a) a first probe and a second probe, wherein the first probe and the second probe are complementary to adjacent sequences of a gDNA analyte, or wherein the first probe and the second probe each comprise a sequence that is substantially complementary to adjacent sequences of the gDNA analyte, and wherein the second probe comprises a 5' FLAP;
    (b) an endonuclease, wherein the endonuclease is capable of cleaving the 5' FLAP from the second probe;
    (c) a substrate comprising a plurality of capture probes, wherein a capture probe of the plurality comprises a spatial barcode and a capture domain; and
    (d) instructions for performing the method of claim 1.

11. The method of claim 1, wherein the 5' FLAP further comprises a functional sequence selected from a primer sequence, a Read 1 sequence, a Read 2 sequence, an index sequence, a P5 index sequence, or a P7 index sequence.

12. The method of claim 1, wherein the second probe further comprises a second barcode.

13. The method of claim 1, further comprising extending the 5' FLAP hybridized to the capture domain.

14. The method of claim 1, wherein the 5' FLAP is about 10 to about 60 nucleotides in length.

15. The method of claim 1, wherein the 5' FLAP comprises a primer sequence.

16. The method of claim 1, wherein the determining step comprises amplifying all or part of the 5' FLAP.

17. The method of claim 1, wherein the determining step comprises sequencing.

18. The method of claim 1, wherein the biological sample is a tissue section.

* * * * *